(12) United States Patent
Fenical et al.

(10) Patent No.: US 7,176,232 B2
(45) Date of Patent: Feb. 13, 2007

(54) SALINOSPORAMIDES AND METHODS FOR USE THEREOF

(75) Inventors: William Fenical, Del Mar, CA (US); Paul Jensen, San Diego, CA (US); Tracy Mincer, San Diego, CA (US); Robert H. R. Feling, Wiesbaden (DE)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/838,157

(22) Filed: Apr. 30, 2004

(65) Prior Publication Data

US 2004/0259856 A1 Dec. 23, 2004

Related U.S. Application Data

(63) Continuation-in-part of application No. 10/600,854, filed on Jun. 20, 2003.

(60) Provisional application No. 60/391,314, filed on Jun. 24, 2002.

(51) Int. Cl.
*C07D 491/044* (2006.01)
*A61K 31/407* (2006.01)
*A61P 35/00* (2006.01)

(52) U.S. Cl. ..................... 514/421; 548/453
(58) Field of Classification Search ............... 548/453; 514/421
See application file for complete search history.

(56) References Cited

U.S. PATENT DOCUMENTS

| | | | |
|---|---|---|---|
| 5,756,764 | A | 5/1998 | Fenteany et al. |
| 6,133,308 | A | 10/2000 | Soucy et al. |
| 6,147,223 | A | 11/2000 | Fenteany et al. |
| 6,214,862 | B1 | 4/2001 | Fenteany et al. |
| 6,294,560 | B1 | 9/2001 | Soucy et al. |
| 6,335,358 | B1 | 1/2002 | Fenteany et al. |
| 6,458,825 | B1 | 10/2002 | Fenteany et al. |
| 6,566,553 | B2 | 5/2003 | Soucy et al. |
| 6,645,999 | B1 | 11/2003 | Schreiber et al. |
| 6,794,516 | B2 | 9/2004 | Soucy et al. |
| 6,838,477 | B2 | 1/2005 | Schreiber et al. |
| 6,849,743 | B2 | 2/2005 | Soucy et al. |
| 2004/0138196 | A1 | 7/2004 | Fenical et al. |
| 2005/0049294 | A1* | 3/2005 | Palladino et al. ............ 514/412 |
| 2005/0203162 | A1* | 9/2005 | Xiao et al. .................. 514/412 |
| 2005/0228186 | A1* | 10/2005 | Corey ......................... 548/453 |
| 2005/0288352 | A1* | 12/2005 | Potts et al. .................. 514/412 |

FOREIGN PATENT DOCUMENTS

| | | |
|---|---|---|
| WO | WO 96/32105 | 10/1996 |
| WO | WO 99/09006 | 2/1999 |
| WO | 02/47610 A2 | 6/2002 |
| WO | WO 2004/071382 A2 | 8/2004 |

OTHER PUBLICATIONS

Golub et al., Science, 286, 531-537, Oct. 1999.*
Feling et al., Angew. (2003) Angew. Chem. Int. Ed. 42(3):355-357.
Fusetani (ed.): *Drugs from the Sea*. Basel, Karger 2000, pp. 6-29.
Goodfellow and Haynes. "Actinomycetes in Marine Sediments" Ortiz-Oritz et al., ed. *Biological, Biochemical, and Biomedical Aspects of Actinomycetes*. Academic Press: Orlando 1984, pp. 453-472.
Davidson, B.S., Current Opinion in Biotechnology 1995, 6:284-291.
Blunt, J.W., et al., Nat. Prod. Rep., 2003, 20:1-48.
Bull, A.T., et al., Microbiol. Mol. Bio. Rev., Sep. 2000, p. 573-606.
Colquhoun, J.A., et al., Extemophiles, 1998, 2:269-277.
Fenical, W., Chem. Rev. 1993, 93:1673-1683.
Fenical, W., Marine Biotechnology 1997, 15:339-341.
Fernandez-Chimeno R.I., et al., Journal of Antibiotics, 2000 53(5):474-478.
Goodfellow and O'Donnell, (1989) Search and discovery of industrially significant actinomycetes, In *Microbial Products: New Approaches, Society for General Microbiology Symposium* No. 44 eds Baumberg, S., et al., pp. 343-383. Cambridge: Cambridge University Press.
Goodfellow and Williams, Ann. Rev. Microbiol. 1983, 37:189-216.
Helmke and Weyland, Int. J. Syst. Bacteriol., 1984, 34(2):127-138.
Horan, A.C. "Aerobic Actinomycetes: A Continuing Source of Novel Natural Products." In Gullo, V.P. (ed.), *The Discovery of Natural Products with Therapeutic Potential*. Boston: Butterworth-Heinemann, 1994, pp. 1-30.

(Continued)

*Primary Examiner*—Fiona T. Powers
(74) *Attorney, Agent, or Firm*—DLA Piper US LLP

(57) ABSTRACT

The present invention is based on the discovery that certain fermentation products of the marine actinomycete strains CNB392 and CNB476 are effective inhibitors of hyperproliferative mammalian cells. The CNB392 and CNB476 strains lie within the family Micromonosporaceae, and the generic epithet *Salinospora* has been proposed for this obligate marine group. The reaction products produced by this strain are classified as salinosporamides, and are particularly advantageous in treating neoplastic disorders due to their low molecular weight, low $IC_{50}$ values, high pharmaceutical potency, and selectivity for cancer cells over fungi.

15 Claims, 17 Drawing Sheets

OTHER PUBLICATIONS

Romero, F., et al., The Journal of Antibiotics, 1997, 50(9):734-737.
Watve, M.G. et al., 2001, Arch. Microbiol 176:386-390.
Weyland, J., Nature, 1969, 223:858.
Zheng, Z, et al., FEMS Microbiology Letters, 2000, 188:87-91.
Jensen, P.R. et al., Appl. Environ. Microbiol., 1991, 57(4):1102-1108.
Mincer, T.J., et al., Appl. Environ. Microbiol., 2002, 68(10):5005-5011.
He, H., et al., J. Am. Chem. Soc., 2001, 123:5362-5363.
Stach, J.E.M., et al., Appl. Environ. Microbiol., 2003, 69(10):6189-6200.
Colquhoun, J.A., et al., Antonie van Leeuwenhoek, 1998, 74:27-40.
Stach, J.E.M., et al., Environ. Microbiol., 2003, 5(10):828-841.
Elliot, P.J. et al., J. Mol. Med., 2003, 81:235-245.
Joseph S.J., et al., 2003, Appl Environ. Microbiol. 69(12):7210-7215.
Otoguro, M., et al., J. Appl. Microbiol., 2001, 92:118-130.
Cheng, X.C., et al., J. Nat. Prod., 1999, 62:608-610.
Cheng, X.C., et al., J. Nat. Prod. 1999, 62:605-607.
Erba, E., et al., British Journal of Cancer, 1999, 88(7):971-980.
Bernan, V.S., et al., Advances in Applied Microbiology 1997, 43:57-90.
Jenson and Fenical, Annu. Rev. Microbiol 1994, 48:559-84.
Okami, Y., Journal of Marine Biotechnology 1993, 1:59-65.
Goodfellow and O'Donnell, (1988) "Actinomycetes in Biotechnology", Okami, et al., ed., *Search and Discovery of New Antibiotics.* Academic Press: San Diego 1988, pp. 33-67.
Moran, M.A., et al., 1995, Appl. environ. Microbiol. 61(10):3695-3700.
Robert H. Feling et al., "Salinosporamide A: A Highly Cytotoxic Proteasome Inhibitor from a Noval Microbial Source, a Marine Bacterium of the New Genus *Salinospora* ", Angew. Chem. Int. Ed. 2003, 42, No. 3, pp. 355-357.
Wiliam Fenical et al., "Marine Microorganisms as a Developing Resource for Drug Discovery", Pharmaceutical News (2002), vol. 9, pp. 489-494.
Giorgio Rivieccio,"Il fondo agli oceani potenti antibiotici e anticancro", Newton, 2003, pp. 1.
Alfred L. Goldberg et al., "Not just research tools—proteasome inhibitors offer therapeutic promise", Nature Medicine, vol. 8, No. 4, Apr. 2002, pp. 338-340.
B.J.R. Nicolaus, "Symbiotic Approach to Drug Design", Decision Making in Drug Research, 1983, pp. 173-186.
Leleti Rajender Reddy et al., "A Simple Sterocontrolled Synthesis of Salinosporamide A", J. Am. Chem. Soc., 2004, vol. 126, pp. 6230-6231.
Fenical et al., "Marine Microorganisms as a Biomedical Source: Are They Unculturable or Uncultured?" PowerPoint Presentation, Center for Marine Biotechnology and Biomedicine (Feb. 24, 2002).
Fenical et al., "*Salinospora*, a Major New Marine Actinomycete Taxon for Drug Discover." PowerPoint Presentation, Center for Marine Biotechnology and Biomedicine (Jun. 24, 2001).

\* cited by examiner

Cytotoxic activity of salinosporamide A (1) and dose response curve

Comp8 (units/ml)

| Sample | Wells | Sample # | OD | Mean Value | Ctr. Avg OD | % Survival | Concentration | IC50 |
|---|---|---|---|---|---|---|---|---|
| Co03 | C8 | 1 | 0.013 | 0.013 | 1.305 | 0.958 | 78.125 | 0.011 |
| Co04 | D8 | 2 | 0.044 | 0.044 | 1.305 | 3.335 | 19.531 | 0.011 |
| Co05 | E8 | 3 | 0.059 | 0.059 | 1.305 | 4.484 | 4.883 | 0.011 |
| Co06 | F8 | 4 | 0.105 | 0.105 | 1.305 | 8.011 | 1.221 | 0.011 |
| Co07 | G8 | 5 | 0.170 | 0.170 | 1.305 | 12.993 | 0.305 | 0.011 |
| Co08 | H8 | 6 | 0.304 | 0.304 | 1.305 | 23.266 | 0.076 | 0.011 |

Standards (mg/ml)

| Sample | Concentration | Back CalcConc | Wells | OD | Mean OD | % Survival | CV % | Ctr. Avg OD | IC50 |
|---|---|---|---|---|---|---|---|---|---|
| Sta03 | 31.250 | Range? | C12 | 0.413 | 0.413 | 31.621 | 0.0 | 1.305 | 0.828 |
| Sta04 | 7.813 | Range? | D12 | 0.542 | 0.542 | 41.510 | 0.0 | 1.305 | 0.828 |
| Sta05 | 1.953 | Range? | E12 | 0.557 | 0.557 | 42.660 | 0.0 | 1.305 | 0.828 |
| Sta06 | 0.488 | Range? | F12 | 0.760 | 0.760 | 58.222 | 0.0 | 1.305 | 0.828 |
| Sta07 | 0.122 | Range? | G12 | 1.287 | 1.287 | 98.620 | 0.0 | 1.305 | 0.828 |
| Sta08 | 0.031 | Range? | H12 | 1.615 | 1.615 | 123.764 | 0.0 | 1.305 | 0.828 |

Smallest standard value: 0.413
Largest standard value: 1.615

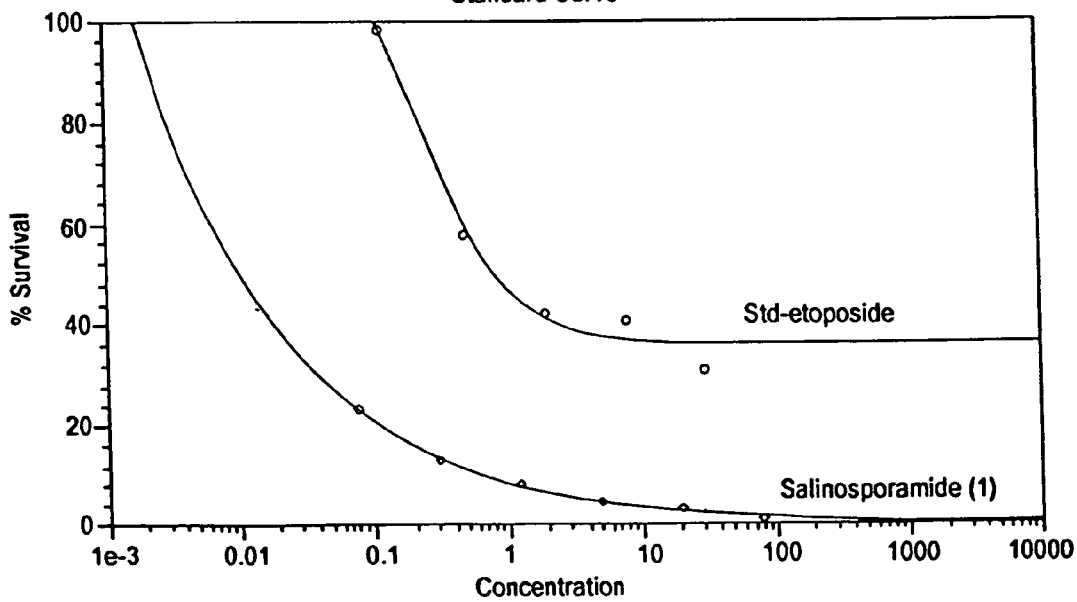

| | A | B | C | D | R^2 |
|---|---|---|---|---|---|
| $y = ((A-D)/(1+(x/C)^B))+D$: | | | | | |
| ○ Comp.8 (Comp8: Concentration vs % Survival) | 2183.255 | 0.398 | 8.34e-7 | 0.073 | 0.997 |
| ○ Std (Standards: Concentration vs % Survival) | 133.236 | 1.227 | 0.192 | 36.119 | 0.993 |

FIG. 4

| Position 16S rDNA | Actinoplanes | Micromonospora | Dactylosporangium | Catellatospora | Pilimelia | Catenuloplanes | Couchioplanes | Spirilliplanes | Verrucosispora | Marinospora |
|---|---|---|---|---|---|---|---|---|---|---|
| 207 | U | U | U | U | C | U | U | U | U | A |
| 219 | C | C | C | C | U | C | C | C | C | U |
| 279 | A | A | A | (A/U) | A | A | A | A | A | G |
| 366 | A | (A/G) | A | A | A | A | A | A | A | C |
| 467 | A | A | (G/A) | A | G | (G/A) | A | A | A | U |
| 468 | A | A | A | A | A | A | A | A | A | U |
| 546 | G | G | G | G | A | G | G | G | G | A |
| 615 | C | (G/C) | C | (U/C) | U | (C/U) | C | C | U | U |
| 1116 | C | C | (C/U) | C | C | C | C | C | C | U |
| 1456 | A | A | A | A | A | A | A | A | A | G |

FIG. 15

SALINOSPORAMIDES AND METHODS FOR USE THEREOF

CROSS REFERENCE TO RELATED APPLICATIONS

This application is a continuation-in-part of U.S. application Ser. No. 10/600,854 filed Jun. 20, 2003, now pending; which claims the benefit under 35 U.S.C. § 119(e) to U.S. Application Ser. No. 60/391,314 filed Jun. 24, 2002, now abandoned. The disclosure of each of the prior applications is considered part of and is incorporated by reference in the disclosure of this application.

GRANT INFORMATION

This invention was made in part with government support under Grant No. CA44848 awarded by the National Institutes of Health, National Caner Institute. The United States government may have certain rights in this invention.

BACKGROUND OF THE INVENTION

1. Field of the Invention

The invention relates generally to anti-neoplastic agents, and more particularly to salinosporamides and their use as anti-neoplastic agents.

2. Background Information

Neoplastic diseases, characterized by the proliferation of cells not subject to the normal control of cell growth, are a major cause of death in humans. Clinical experience in chemotherapy has demonstrated that new and more effective cytotoxic drugs are desirable to treat these diseases. Indeed, the use of anti-neoplastic agents has increased due to the identification of new neoplasms and cancer cell types with metastases to different areas, and due to the effectiveness of antineoplastic treatment protocols as a primary and adjunctive medical treatment for cancer.

Since anti-neoplastic agents are cytotoxic (poisonous to cells) they not only interfere with the growth of tumor cells, but those of normal cells. Anti-neoplastic agents have more of an effect on tumor cells than normal cells because of their rapid growth. Thus, normal tissue cells that are affected by anti-neoplastic agents are rapidly dividing cells, such as bone marrow (seen in low blood counts), hair follicles (seen by way of hair loss) and the GI mucosal epithelium (accounting for nausea, vomiting, loss of appetite, diarrhea). In general, anti-neoplastic agents have the lowest therapeutic indices of any class of drugs used in humans and hence produce significant and potentially life-threatening toxicities. Certain commonly-used anti-neoplastic agents have unique and acute toxicities for specific tissues. For example, the vinca alkaloids possess significant toxicity for nervous tissues, while adriamycin has specific toxicity for heart tissue and bleomycin has for lung tissue.

Thus, there is a continuing need for anti-neoplastic agents that are effective in inhibiting the proliferation of hyperproliferative cells while also exhibiting $IC_{50}$ values lower than those values found for current anti-neoplastic agents, thereby resulting in marked decrease in potentially serious side effects.

SUMMARY OF THE INVENTION

The present invention is based on the discovery that certain fermentation products of the marine actinomycete strains CNB392 and CNB476 are effective inhibitors of hyperproliferative mammalian cells. The CNB392 and CNB476 strains lie within the family Micromonosporaceae, and the generic epithet *Salinospora* has been proposed for this obligate marine group. The reaction products produced by this strain are classified as salinosporamides, and are particularly advantageous in treating neoplastic disorders due to their low molecular weight, low $IC_{50}$ values, high pharmaceutical potency, and selectivity for cancer cells over fungi.

In one embodiment of the invention, there is provided compounds having the structure (I):

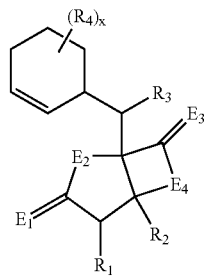

I wherein:
  $R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;
  Each $R_4$ is independently alkyl, substituted alkyl, alkenyl, substituted alkenyl, alkynyl, substituted alkynyl, aryl, substituted aryl, cycloalkyl, substituted cycloalkyl;
  $E_1$ to $E_4$ are each independently —O—, —NR$_5$—, or —S—, wherein $R_5$ is —H or $C_1$–$C_6$ alkyl; and
  x is 0 to 8.

In a further embodiment of the invention, there are provided compounds having the structure (II):

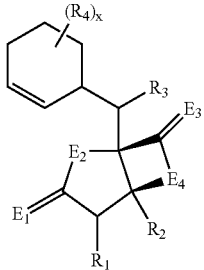

II wherein:
  $R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

Each $R_4$ is independently alkyl, substituted alkyl, alkenyl, substituted alkenyl, alkynyl, substituted alkynyl, aryl, substituted aryl, cycloalkyl, substituted cycloalkyl;

$E_1$ to $E_4$ are each independently —O, —$NR_5$, or —S, wherein $R_5$ is —H or $C_1$–$C_6$ alkyl; and x is 0 to 8.

In another embodiment of the invention, there are provided compounds having the structure (III):

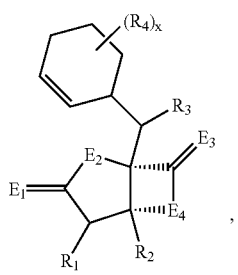

III wherein:

$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl, each $R_4$ is independently alkyl, substituted alkyl, alkenyl, substituted alkenyl, alkynyl, substituted alkynyl, aryl, substituted aryl, cycloalkyl, substituted cycloalkyl, $E_1$ to $E_4$ are each independently —O, —$NR_5$, or —S, wherein $R_5$ is —H or $C_1$–$C_6$ alkyl, and x is 0 to 8.

In still a further embodiment of the invention, there are provided compounds having the structure (IV):

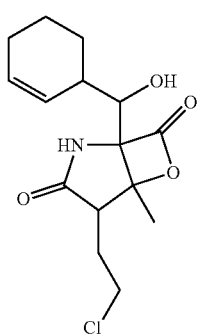

IV

In a further embodiment of the invention, there are provided compounds having the structure (V):

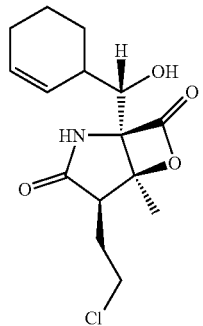

V

In a further embodiment of the invention, there are provided compounds having the structure (VI):

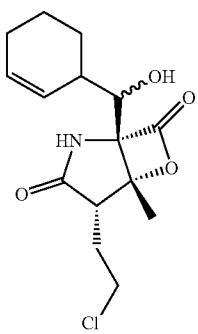

VI

In another embodiment, there are provided pharmaceutical compositions including at least one compound of structures I–VI in a pharmaceutically acceptable carrier therefor.

In another embodiment, there are provided articles of manufacture including packaging material and a pharmaceutical composition contained within the packaging material, wherein the packaging material includes a label which indicates that the pharmaceutical composition can be used for treatment of cell proliferative disorders and wherein the pharmaceutical composition includes at least one compound of structures I–VI.

In yet another embodiment, there are provided methods for treating a mammalian cell proliferative disorder. Such a method can be performed for example, by administering to a subject in need thereof a therapeutically effective amount of a compound having structures I–VI.

In an additional embodiment, there are provided methods for producing a compound of structures I–VI having the ability to inhibit the proliferation of hyperproliferative mammalian cells. Such a method can be performed, for example, by cultivating a culture of a *Salinospora* sp. strains CNB392 or CNB476 (ATCC # PTA-5275, deposited on Jun. 20, 2003, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A.) and isolating from the culture at least one compound of structure I.

BRIEF DESCRIPTION OF THE DRAWINGS

FIG. 4 compares the cytotoxic activity and dose response curves of Salinosporamide A and Etoposide.

FIG. 15 sets forth the signature nucleotides that strains CNB392 and CNB476 possess within their 16 S rDNA, which separate these strains phylogenetically from all other family members of the family Micromonosporaceae.

DETAILED DESCRIPTION OF THE INVENTION

Figure 1:
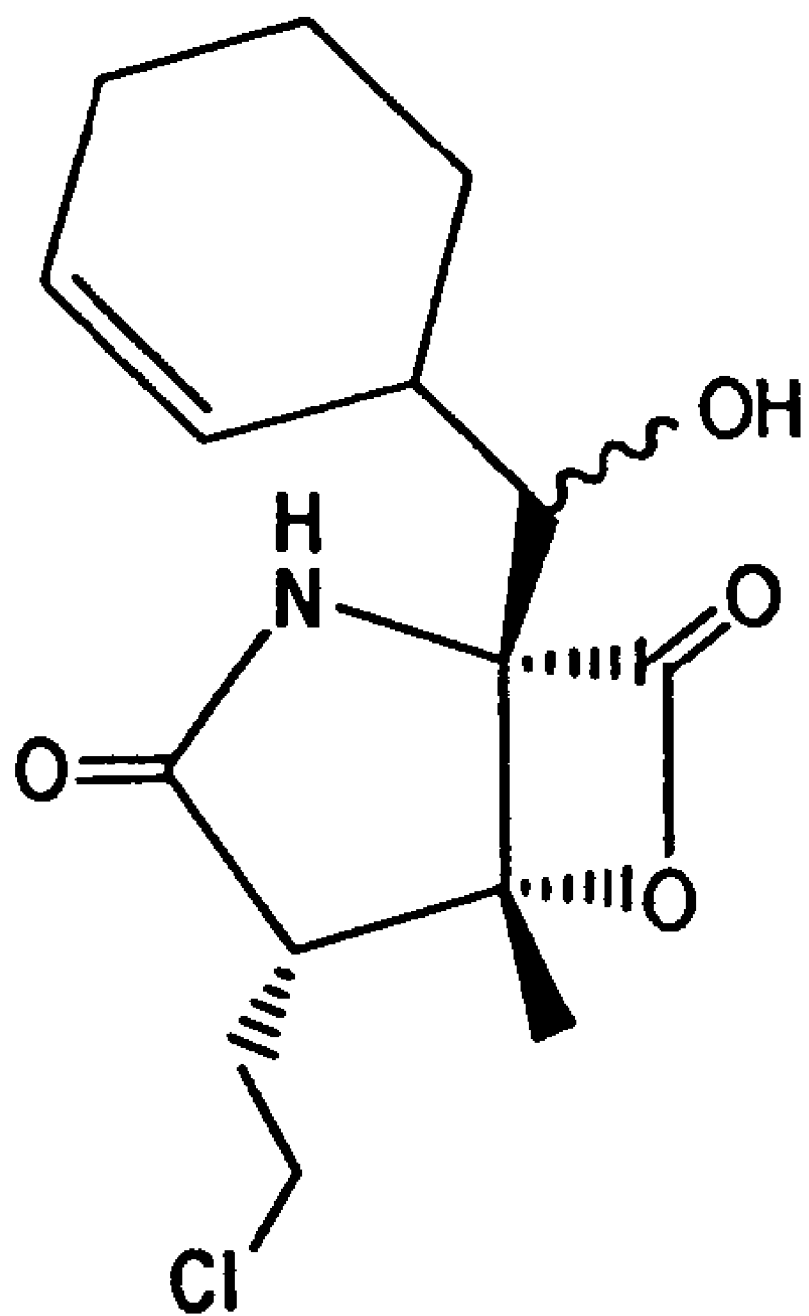
FIG. 1 depicts the chemical structure of an exemplary compound of the invention, Salinosporamide A, with relative stereochemistry.

In one embodiment, there are provided compounds having the structure (I):

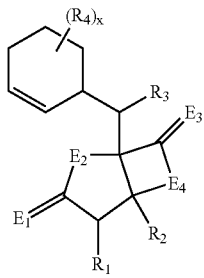

I wherein:
$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

Each $R_4$ is independently alkyl, substituted alkyl, alkenyl, substituted alkenyl, alkynyl, substituted alkynyl, aryl, substituted aryl, cycloalkyl, substituted cycloalkyl;

$E_1$ to $E_4$ are each independently —O, —$NR_5$, or —S, wherein $R_5$ is —H or $C_1$–$C_6$ alkyl; and x is 0 to 8.

In a further embodiment of the invention, there are provided compounds having the structure (II):

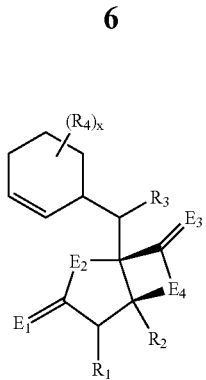

II wherein:
$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl;

Each $R_4$ is independently alkyl, substituted alkyl, alkenyl, substituted alkenyl, alkynyl, substituted alkynyl, aryl, substituted aryl, cycloalkyl, substituted cycloalkyl;

$E_1$ to $E_4$ are each independently —O, —$NR_5$, or —S, wherein $R_5$ is —H or $C_1$–$C_6$ alkyl; and x is 0 to 8.

In one embodiment, there are provided compounds having the structure (III):

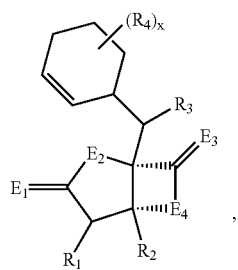

III wherein:
$R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonyl, sulfonamide, or sulfuryl, each $R_4$ is independently alkyl, substituted alkyl, alkenyl, substituted alkenyl, alkynyl, substituted alkynyl, aryl, substituted aryl, cycloalkyl, substituted cycloalkyl, $E_1$ to $E_4$ are each independently —O, —$NR_5$, or —S, wherein $R_5$ is —H or $C_1$–$C_6$ alkyl, and x is 0 to 8.

In still a further embodiment of the invention, there are provided compounds having the structure (IV):

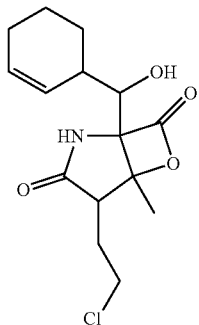

In a further embodiment of the invention, there are provided compounds having the structure (V):

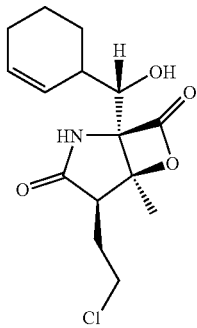

In a further embodiment of the invention, there are provided compounds having the structure (VI):

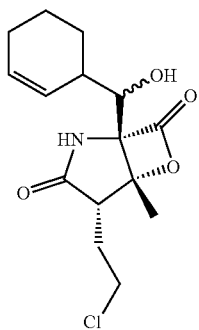

As used herein, the term "alkyl" refers to a monovalent straight or branched chain hydrocarbon group having from one to about 12 carbon atoms, including methyl, ethyl, n-propyl, isopropyl, n-butyl, isobutyl, tert-butyl, n-hexyl, and the like.

As used herein, "substituted alkyl" refers to alkyl groups further bearing one or more substituents selected from hydroxy, alkoxy, mercapto, cycloalkyl, substituted cycloalkyl, heterocyclic, substituted heterocyclic, aryl, substituted aryl, heteroaryl, substituted heteroaryl, aryloxy, substituted aryloxy, halogen, cyano, nitro, amino, amido, —C(O)H, acyl, oxyacyl, carboxyl, sulfonyl, sulfonamide, sulfuryl, and the like.

As used herein, "lower alkyl" refers to alkyl groups having from 1 to about 6 carbon atoms.

As used herein, "alkenyl" refers to straight or branched chain hydrocarbyl groups having one or more carbon-carbon double bonds, and having in the range of about 2 up to 12 carbon atoms, and "substituted alkenyl" refers to alkenyl groups further bearing one or more substituents as set forth above.

As used herein, "alkynyl" refers to straight or branched chain hydrocarbyl groups having at least one carbon-carbon triple bond, and having in the range of about 2 up to 12 carbon atoms, and "substituted alkynyl" refers to alkynyl groups further bearing one or more substituents as set forth above.

As used herein, "aryl" refers to aromatic groups having in the range of 6 up to 14 carbon atoms and "substituted aryl" refers to aryl groups further bearing one or more substituents as set forth above.

As used herein, "heteroaryl" refers to aromatic rings containing one or more heteroatoms (e.g., N, O, S, or the like) as part of the ring structure, and having in the range of 3 up to 14 carbon atoms and "substituted heteroaryl" refers to heteroaryl groups further bearing one or more substituents as set forth above.

As used herein, "alkoxy" refers to the moiety —O-alkyl-, wherein alkyl is as defined above, and "substituted alkoxy" refers to alkoxyl groups further bearing one or more substituents as set forth above.

As used herein, "thioalkyl" refers to the moiety —S-alkyl-, wherein alkyl is as defined above, and "substituted thioalkyl" refers to thioalkyl groups further bearing one or more substituents as set forth above.

As used herein, "cycloalkyl" refers to ring-containing alkyl groups containing in the range of about 3 up to 8 carbon atoms, and "substituted cycloalkyl" refers to cycloalkyl groups further bearing one or more substituents as set forth above.

As used herein, "heterocyclic", refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

In certain embodiments, there are provided compounds of structures I–III wherein $E_1$, $E_3$, and $E_4$ are —O, and $E_2$ is —NH.

In certain embodiments, there are provided compounds of structures I–III wherein $R_1$ and $R_2$ are —H, alkyl, or substituted alkyl, and $R_3$ is hydroxy or alkoxy. In some embodiments, $R_1$ is substituted alkyl. Exemplary substituted alkyls contemplated for use include halogenated alkyls, such as for example chlorinated alkyls.

The compounds of the invention may be formulated into pharmaceutical compositions as natural or salt forms. Pharmaceutically acceptable non-toxic salts include the base addition salts (formed with free carboxyl or other anionic groups) which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, p-toluenesulfonic, methanesulfonic acid, oxalic, tartaric, mandelic, and the like. Salts of the invention include amine salts formed by the protonation of an amino group with inorganic acids such as hydrochloric acid, hydrobromic acid, hydroiodic acid, sulfuric acid, phosphoric acid, and the like. Salts of the invention also include amine salts formed by the protonation of an amino group with suitable organic acids, such as p-toluenesulfonic acid, acetic acid, and the like. Additional excipients which are contemplated for use in the practice of the present invention are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference.

The compounds according to this invention may contain one or more asymmetric carbon atoms and thus occur as racemates and racemic mixtures, single enantiomers, diastereomeric mixtures and individual diastereomers. The term "stereoisomer" refers to chemical compounds which differ from each other only in the way that the different groups in the molecules are oriented in space. Stereoisomers have the same molecular weight, chemical composition, and constitution as another, but with the atoms grouped differently. That is, certain identical chemical moieties are at different orientations in space and, therefore, when pure, have the ability to rotate the plane of polarized light. However, some pure stereoisomers may have an optical rotation that is so slight that it is undetectable with present instrumentation. All such isomeric forms of these compounds are expressly included in the present invention.

Each stereogenic carbon may be of R or S configuration. Although the specific compounds exemplified in this application may be depicted in a particular configuration, compounds having either the opposite stereochemistry at any given chiral center or mixtures thereof are also envisioned. When chiral centers are found in the derivatives of this invention, it is to be understood that this invention encompasses all possible stereoisomers. The terms "optically pure compound" or "optically pure isomer" refers to a single stereoisomer of a chiral compound regardless of the configuration of the compound.

Exemplary invention compounds of structure I are shown below:

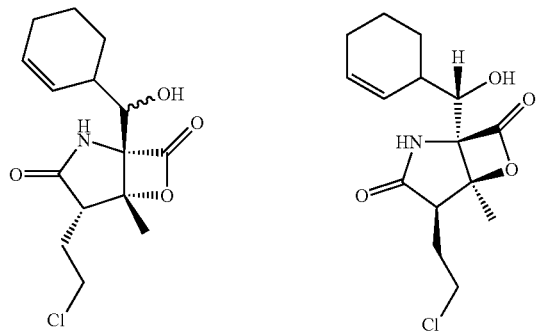

Salinosporamide A exhibits a molecular structure having a variety of functional groups (lactone, alkylhalide, amide, hydroxide) that can be chemically modified to produce synthetic derivatives. Accordingly, exemplary invention compound Salinosporamide A provides an excellent lead structure for the development of synthetic and semisynthetic derivatives. Indeed, Salinosporamide A can be derivatized to improve pharmacokinetic and pharmacodynamic properties, which facilitate administration and increase utility of the derivatives as anti-neoplastic agents. Procedures for chemically modifying invention salinosporamide compounds to produce additional compounds within the scope of the present invention are available to those of ordinary skill in the art.

Figure 3:
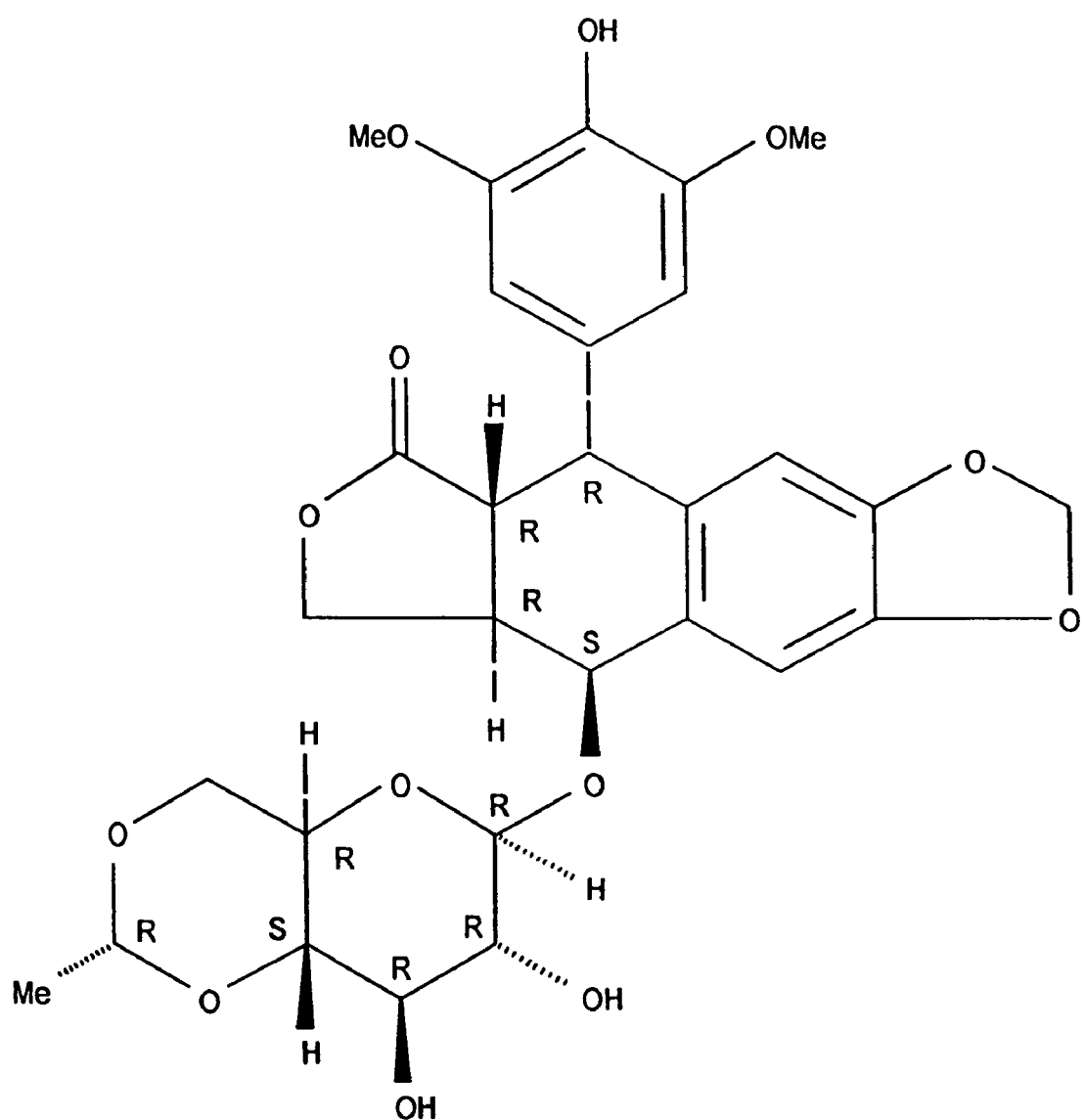
FIG. 3 depicts the chemical structure of Etoposide, an anti-neoplastic agent in therapy against several human cancers.

Salinosporamide A shows strong cytotoxic activity against human colon cancer cells in the HTC-116 cell assays. The $IC_{50}$ of 11 ng/mL exceeds the activity of etoposide (see FIG. 3, $IC_{50}$ 828 ng/mL), an anticancer drug used for treatment of a number of cancers, by almost two orders of magnitude (see FIG. 4). This high activity makes invention salinosporamides excellent candidates for use in the treatment of various human cancers, especially slow growing, refractile cancers for which there are no therapies. Salinosporamide A is specific to inhibition of mammalian cells and shows little anifungal activity against *Candida albicans* ($IC_{50}$ 250 µg/mL) and no antibacterial activity (*Staphylococcus aureus, Enterococcus faecium*). The $IC_{50}$ of Salinosporamide A is far lower than the strongest chemotherapeutic agents currently in use or in clinical trials.

Salinosporamide A is a fermentation product of the marine actinomycete strains CN8392 and CNB476. These strains are members of the order Actinomycetales, which are high G+C gram positive bacteria. The novelty of CNB392 and CNB476 is at the genus level. Invention compounds set forth herein are produced by certain "*Salinospora*" sp. In some embodiments, invention compounds are produced by "*Salinospora*" sp. strains CNB392 and CNB476. To that end, the CNB476 strains of "*Salinospora*" sp. were deposited on Jun. 20, 2003, pursuant to the Budapest Treaty on the International Deposit of Microorganisms for the Purposes of Patent Procedure with the Patent Culture Depository of the American Type Culture Collection, 12301 Parklawn Drive, Rockville, Md. 20852 U.S.A. under ATCC Accession No. PTA-5275.

As is the case with other organisms, the characteristics of "*Salinospora*" sp. are subject to variation. For example, recombinants, variants, or mutants of the specified strain may be obtained by treatment with various known physical and chemical mutagens, such as ultraviolet ray, X-rays, gamma rays, and N-methyl-N'-nitro-N-nitrosoguanidine. All natural and induced variants, mutants, and recombinants of the specified strain which retain the characteristic of producing a compound of the invention are intended to be within the scope of the claimed invention.

Invention compounds can be prepared, for example, by bacterial fermentation, which generates the compounds in sufficient amounts for pharmaceutical drug development and for clinical trials. In some embodiments, invention compounds are produced by fermentation of the actinomycete strains CNB392 and CNB476 in AlBfe+C or CKA-liquid media. Essential trace elements which are necessary for the growth and development of the culture should also be included in the culture medium. Such trace elements commonly occur as impurities in other constituents of the medium in amounts sufficient to meet the growth requirements of the organisms. It may be desirable to add small amounts (i.e. 0.2 mL/L) of an antifoam agent such as polypropylene glycol (M.W. about 2000) to large scale cultivation media if foaming becomes a problem. The organic metabolites are isolated by adsorption onto an amberlite XAD-16 resin. For example, Salinosporamide A is isolated by elution of the XAD-16 resin with methanol: dichlormethane 1:1, which affords about 105 mg crude extract per liter of culture. Salinosporamide A is then isolated from the crude extract by reversed-phase flash chromatography followed by reverse-phase HPLC and normal phase HPLC, which yields 6.7 mg of Salinosporamide A.

Figure 5:
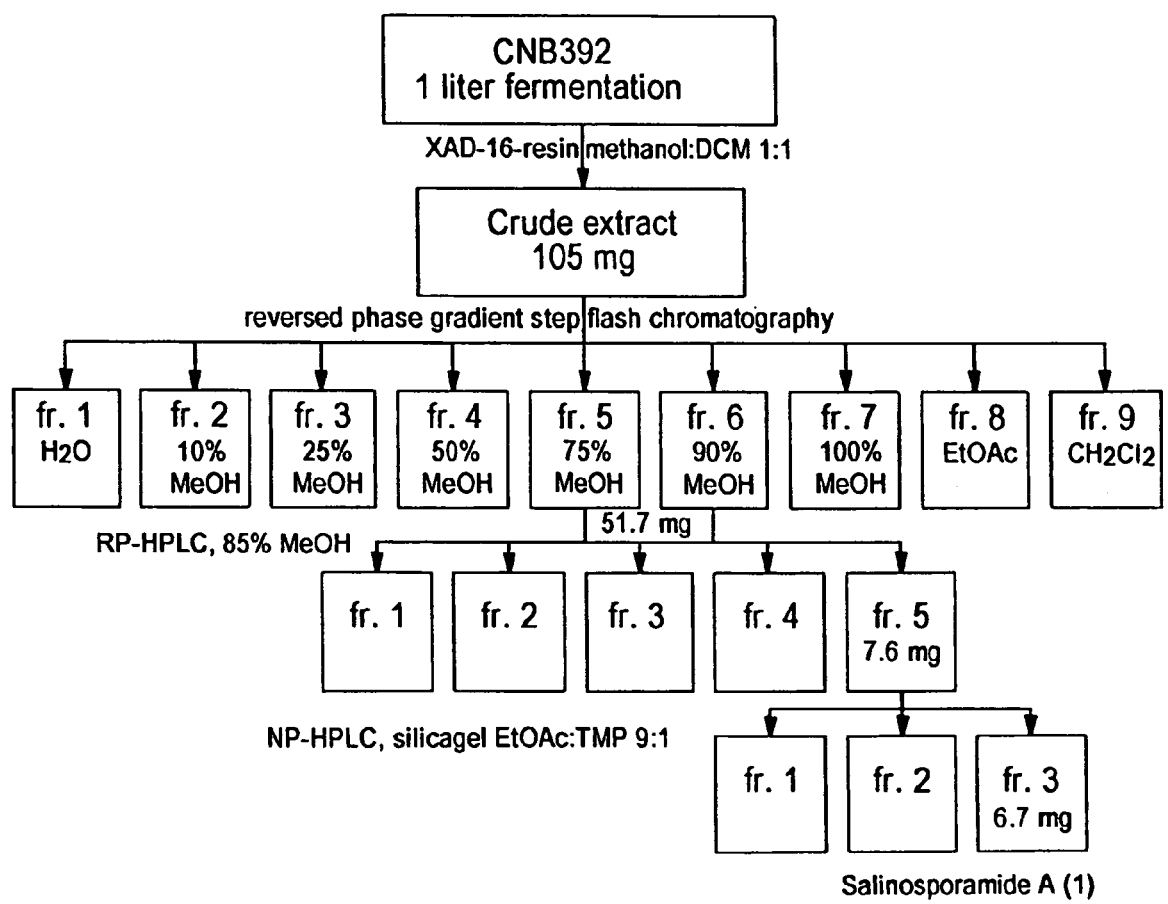
FIG. 5 is a block diagram depicting an exemplary separation scheme used to isolate Salinosporamide A.
Figure 6:
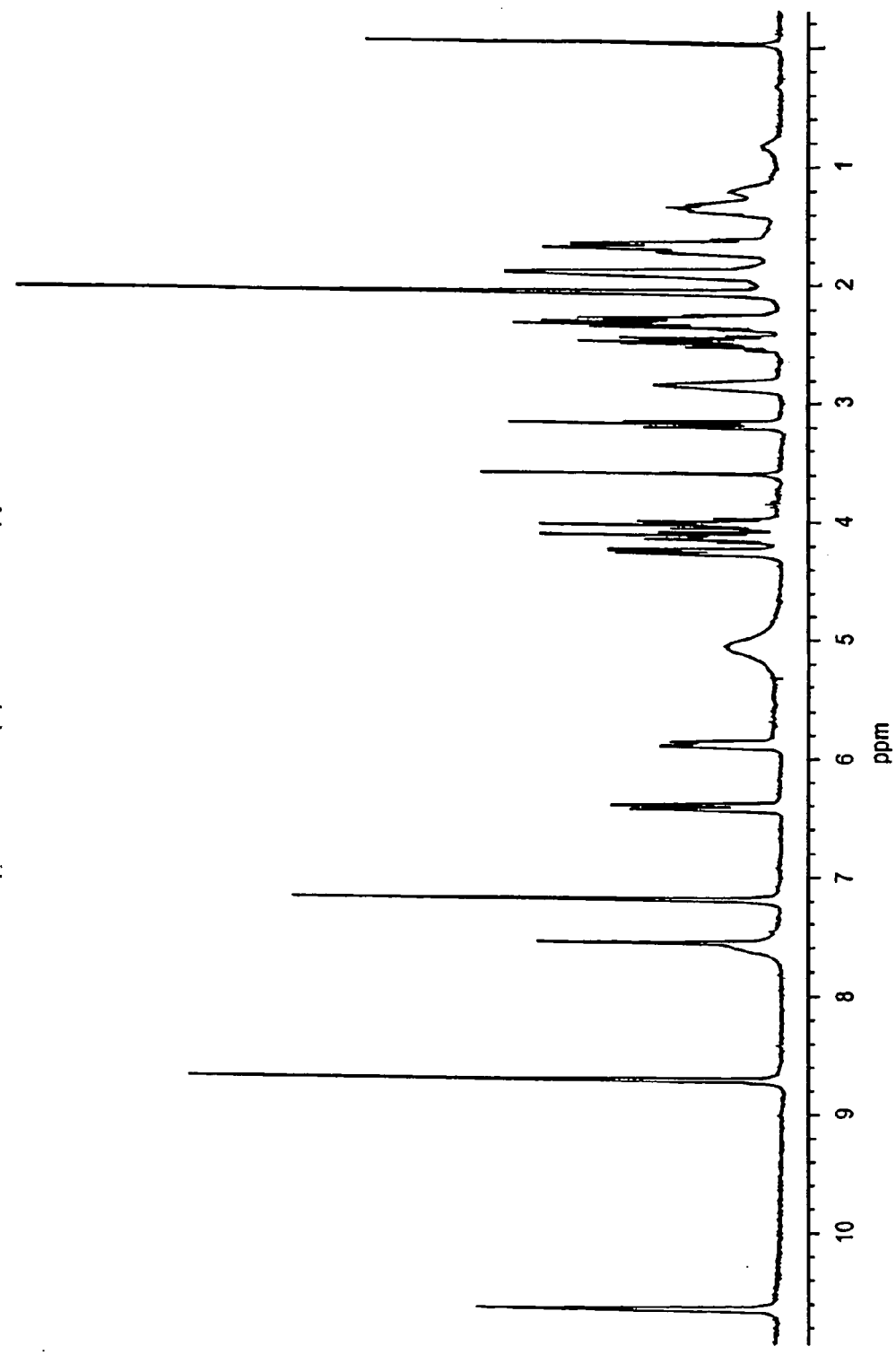
FIGS. 6–14 set forth NMR, IR, and UV spectroscopic data used to elucidate the structure of Salinosporamide A.
Figure 7:
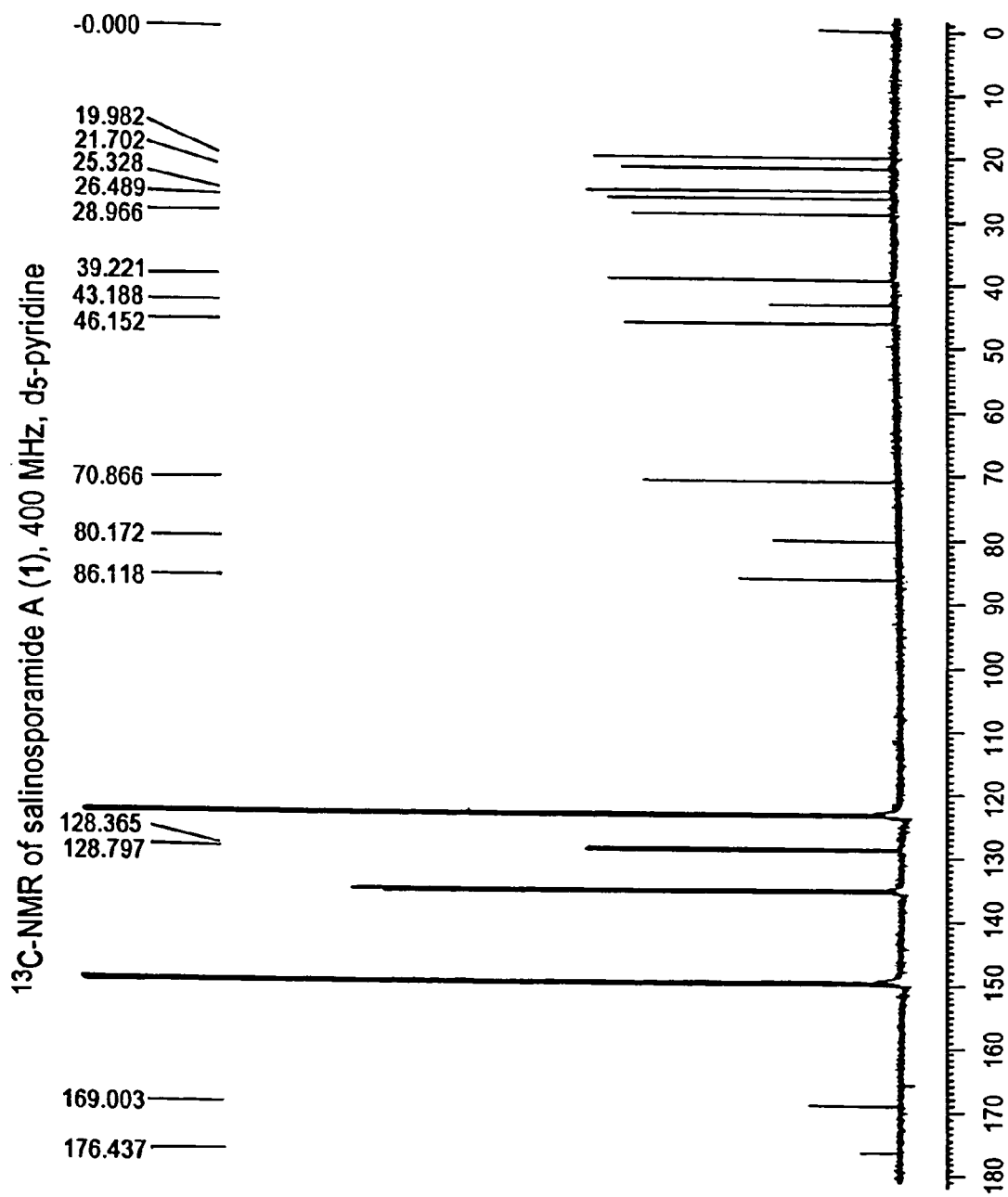
Figure 8:
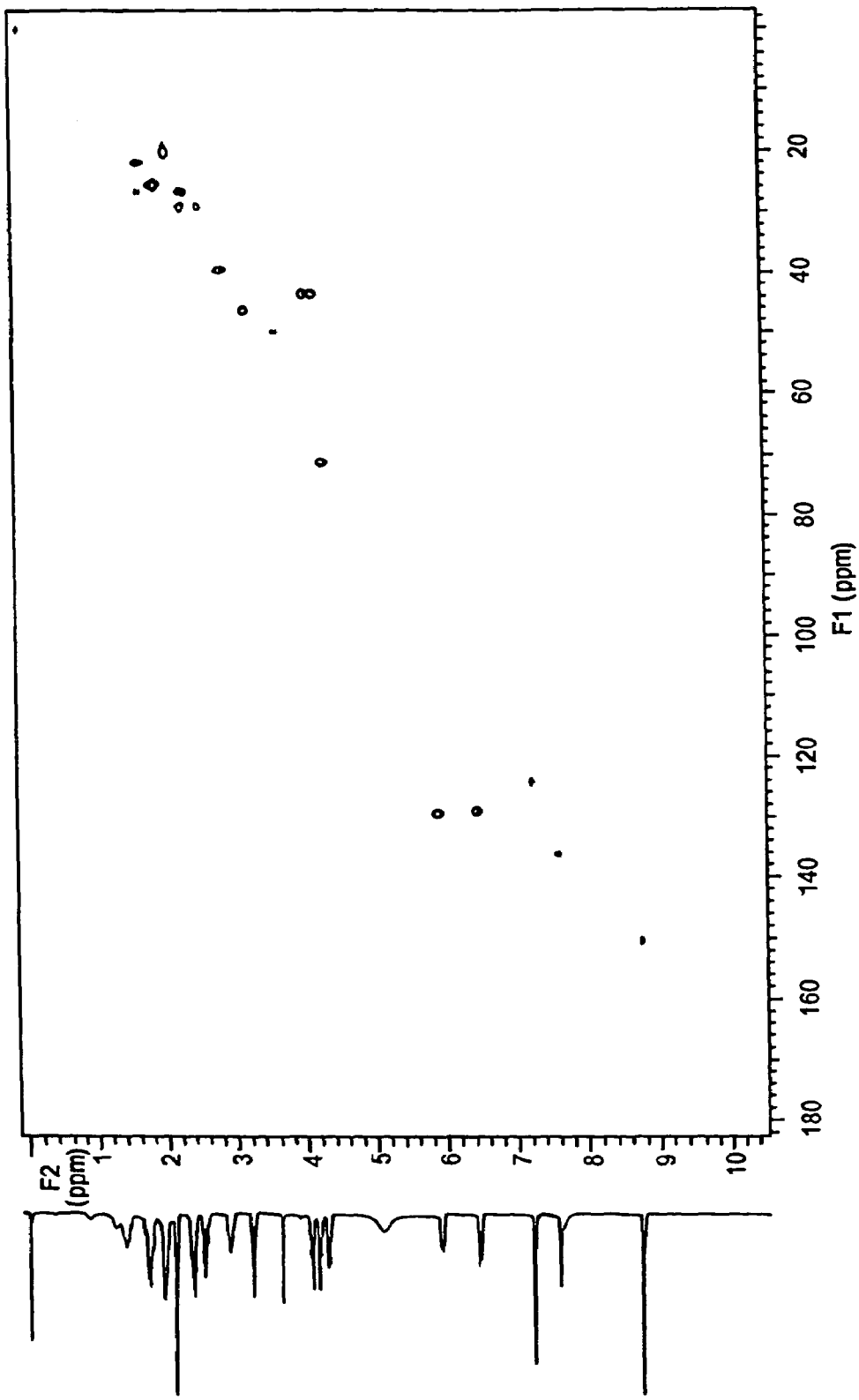
Figure 9:
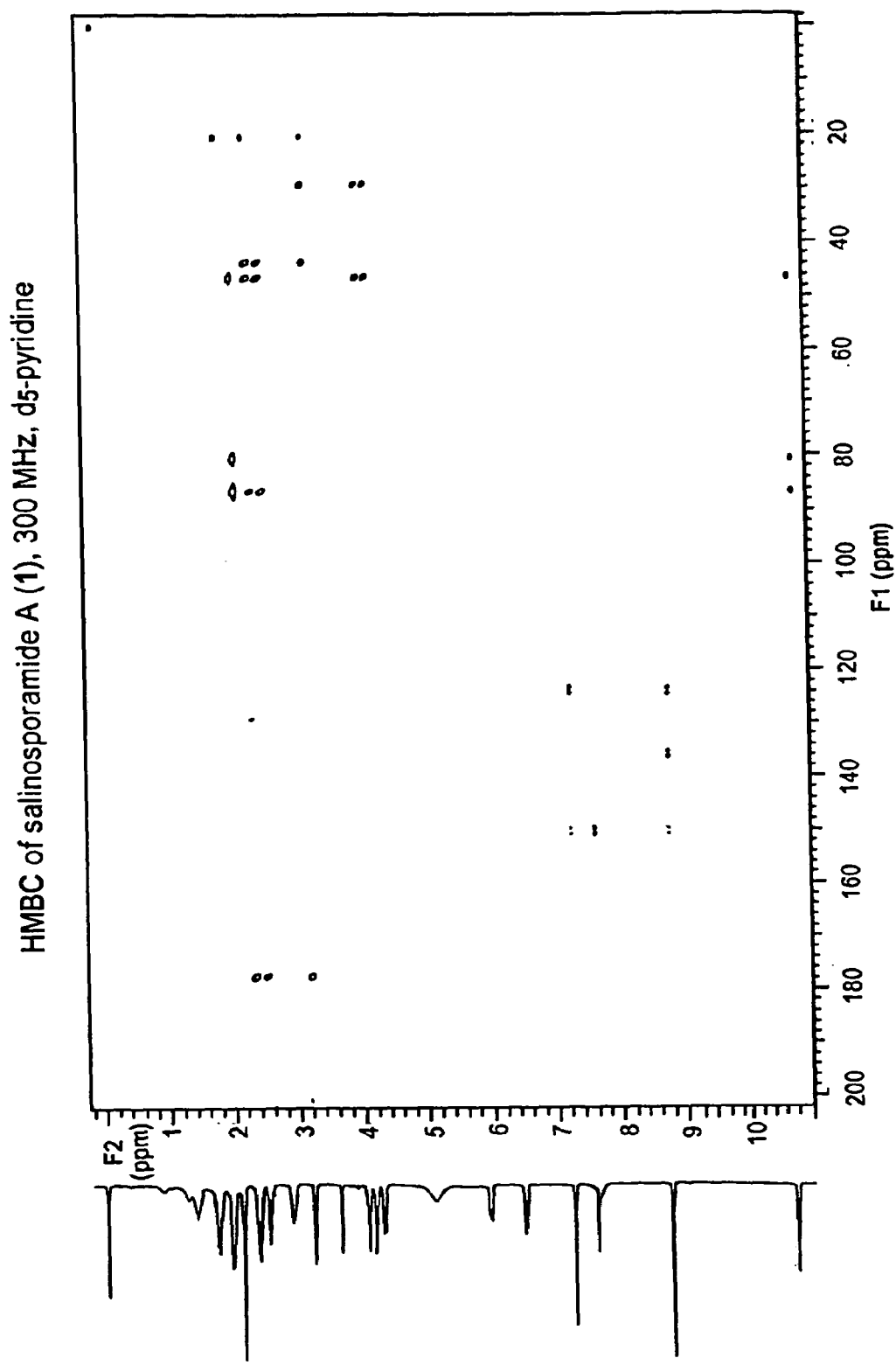
Figure 10:
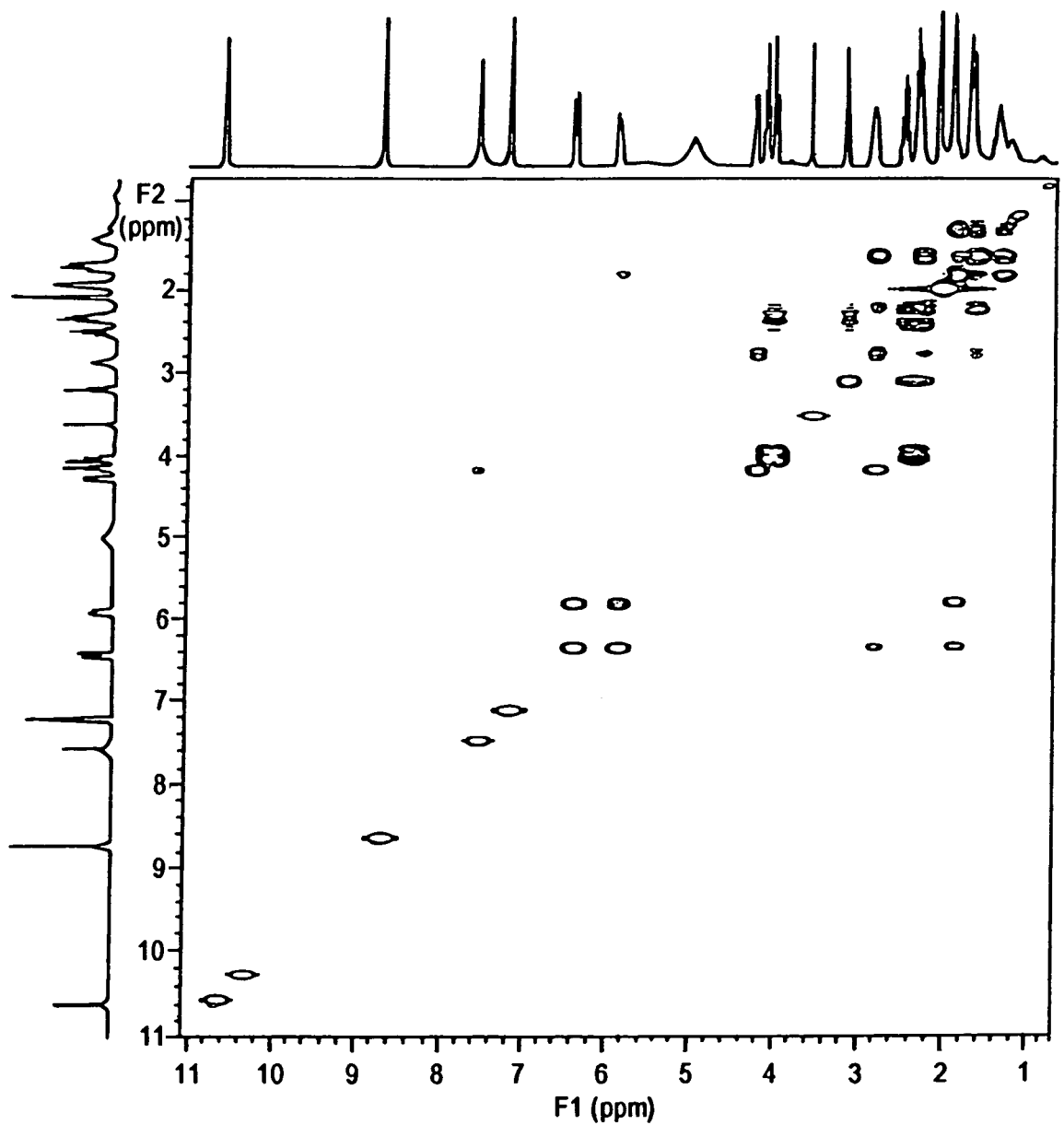
Figure 11:
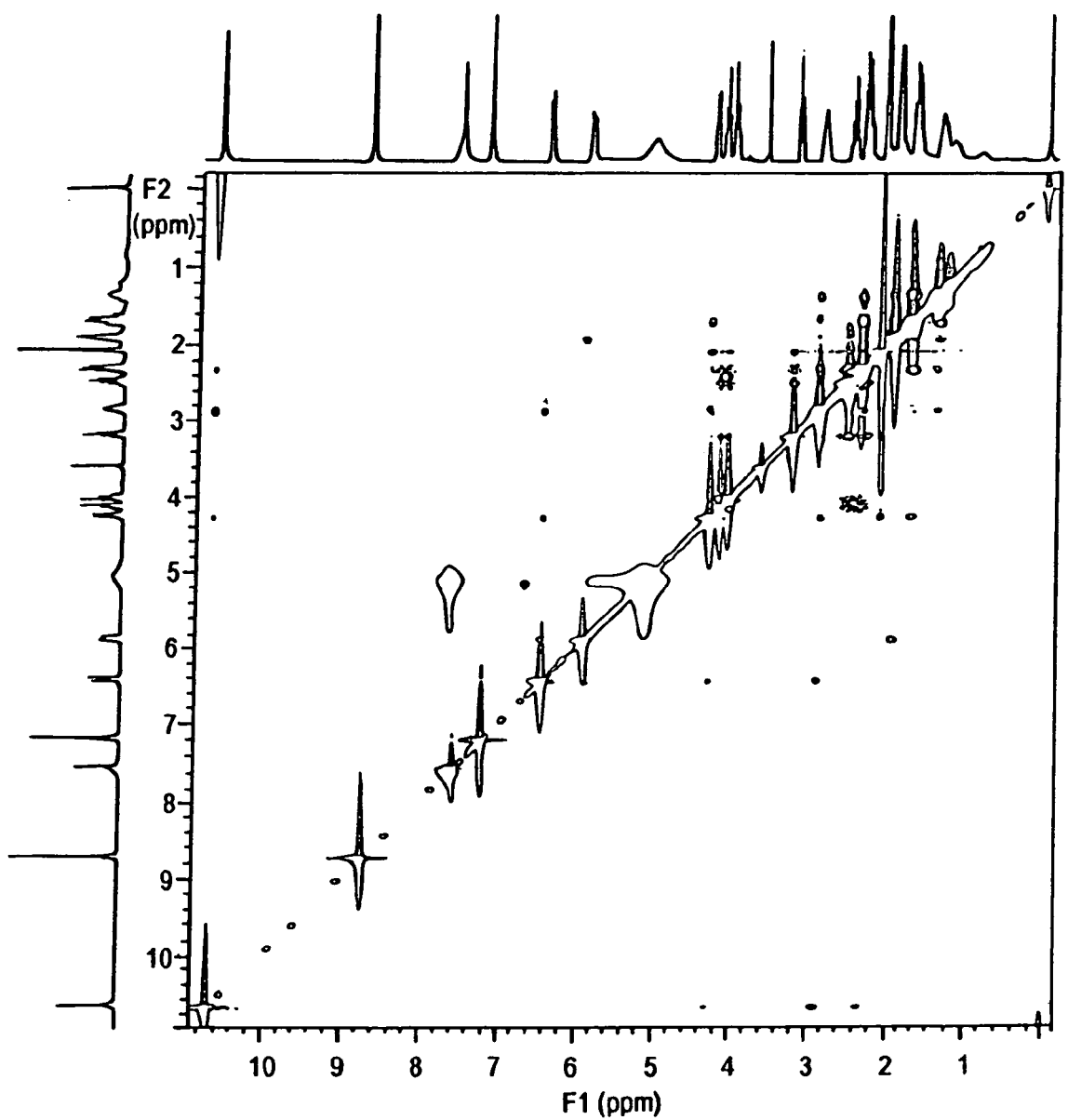
Figure 12:
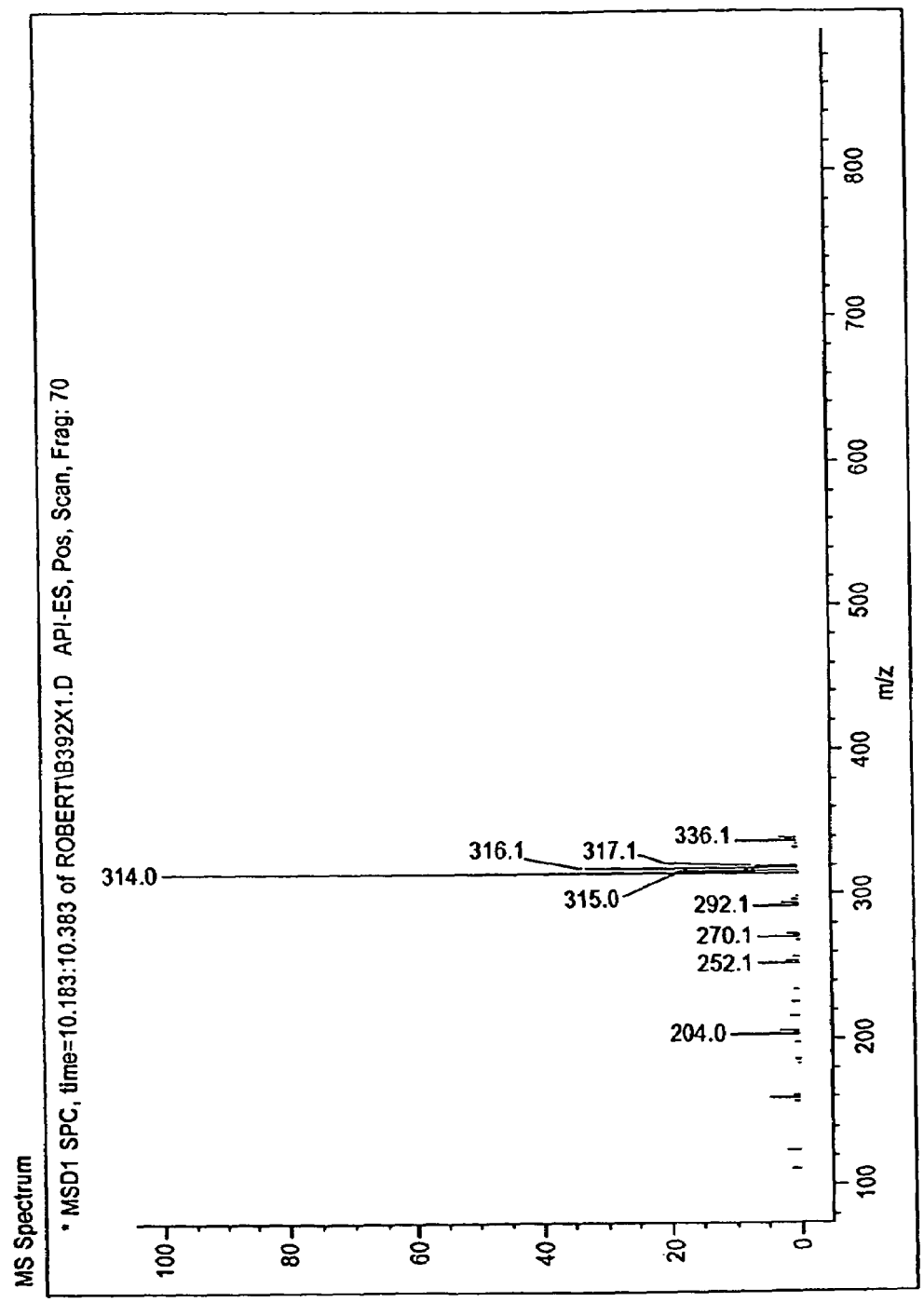
Figure 13:
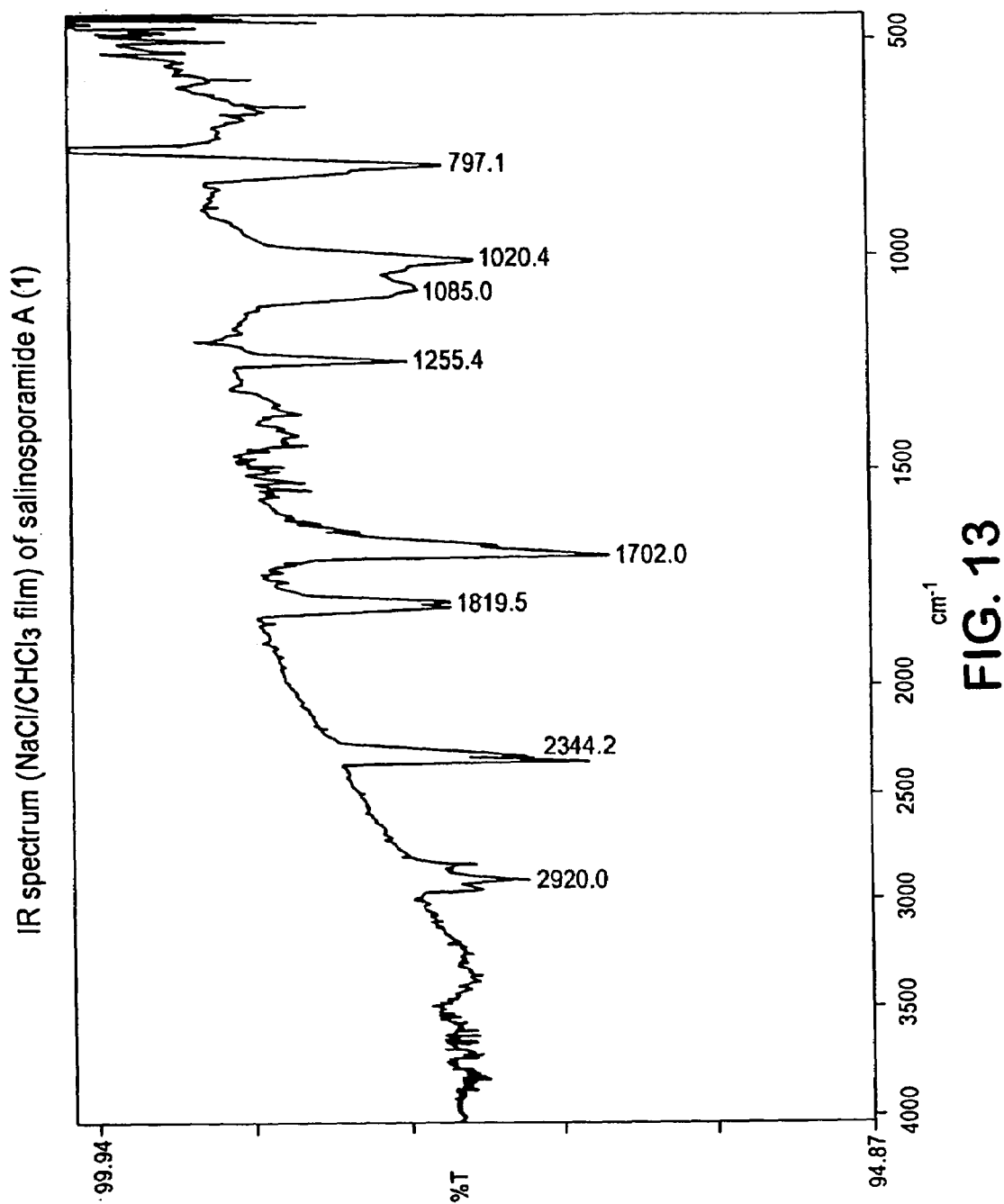
Figure 14:
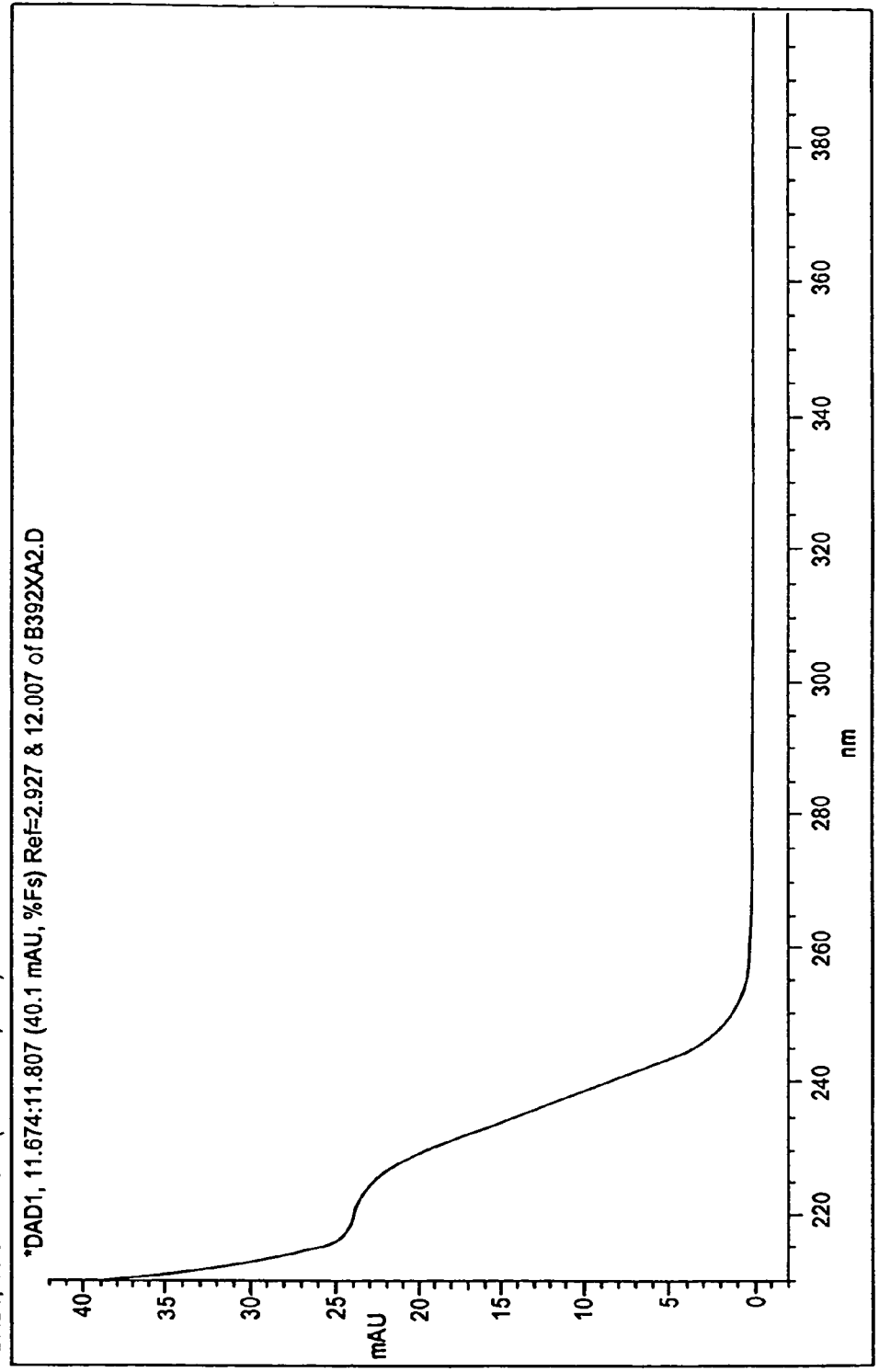

FIG. 5 sets forth a block diagram outlining isolation and separation protocols for invention compounds.

The structure of Salinosporamide A was elucidated by a variety of NMR techniques, mass spectroscopy, IR, and UV spectroscopy, as set forth in FIGS. 6–14.

The absolute structure of salinosporamide A, and confirmation of the overall structure of salinosporamide A, was achieved by single-crystal X-ray diffraction analysis (see Example 3).

The present invention also provides articles of manufacture including packaging material and a pharmaceutical composition contained within the packaging material, wherein the packaging material comprises a label which indicates that the pharmaceutical composition can be used for treatment of disorders and wherein the pharmaceutical composition includes a compound according to the present invention. Thus, in one aspect, the invention provides a pharmaceutical composition including a compound of the invention, wherein the compound is present in a concentration effective to treat cell proliferative disorders. The concentration can be determined by one of skill in the art according to standard treatment regimen or as determined by an in vivo animal assay, for example.

Pharmaceutical compositions employed as a component of invention articles of manufacture can be used in the form of a solid, a solution, an emulsion, a dispersion, a micelle, a liposome, and the like, wherein the resulting composition contains one or more invention compounds as an active ingredient, in admixture with an organic or inorganic carrier or excipient suitable for enteral or parenteral applications. Compounds employed for use as a component of invention articles of manufacture may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used.

The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

Invention pharmaceutical compositions may be administered by any suitable means, for example, orally, such as in the form of tablets, capsules, granules or powders; sublingually; buccally; parenterally, such as by subcutaneous, intravenous, intramuscular, or intracisternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. Invention compounds may, for example, be administered in a form suitable for immediate release or extended release. Immediate release or extended release may be achieved by the use of suitable pharmaceutical compositions comprising invention compounds, or, particularly in the case of extended release, by the use of devices such as subcutaneous implants or osmotic pumps. Invention compounds may also be administered liposomally.

The invention further provides methods for using invention salinosporamide compounds of structures (I)–(VI) to inhibit the proliferation of mammalian cells by contacting these cells with an invention salinosporamide compound in an amount sufficient to inhibit the proliferation of the mammalian cell. One embodiment is a method to inhibit the proliferation of hyperproliferative mammalian cells. For purposes of this invention, "hyperproliferative mammalian cells" are mammalian cells which are not subject to the characteristic limitations of growth, e.g., programmed cell death (apoptosis). A further preferred embodiment is when the mammalian cell is human. The invention further provides contacting the mammalian cell with at least one invention salinosporamide compound and at least one additional anti-neoplastic agent.

In another embodiment, there are provided methods for treating a mammalian cell proliferative disorder, comprising administering to a subject in need thereof a therapeutically effective amount of a compound of structures (I)–(VI). Cell proliferative disorders that can be effectively treated by the methods of the invention include disorders characterized by the formation of neoplasms. As such, invention compounds are anti-neoplastic agents. As used herein, "neoplastic" pertains to a neoplasm, which is an abnormal growth, such growth occurring because of a proliferation of cells not subject to the usual limitations of growth. As used herein, "anti-neoplastic agent" is any compound, composition, admixture, co-mixture or blend which inhibits, eliminates, retards or reverses the neoplastic phenotype of a cell. In certain embodiments, the neoplasms are selected from mammory, small-cell lung, non-small-cell lung, colorectal, leukemia, melanoma, pancreatic adenocarcinoma, central nervous system (CNS), ovarian, prostate, sarcoma of soft tissue or bone, head and neck, gastric which includes thyroid and non-Hodgkin's disease, stomach, myeloma, bladder, renal, neuroendocrine which includes thyroid and non-Hodgkin's disease and Hodgkin's disease neoplasms. In one embodiment, the neoplasms are colorectal.

Chemotherapy, surgery, radiation therapy, therapy with biologic response modifiers, and immunotherapy are currently used in the treatment of cancer. Each mode of therapy has specific indications which are known to those of ordinary skill in the art, and one or all may be employed in an attempt to achieve total destruction of neoplastic cells. Chemotherapy utilizing one or more invention salinosporamide compounds is provided by the present invention. Moreover, combination chemotherapy, chemotherapy utilizing invention salinosporamide compounds in combination with other neoplastic agents, is also provided by the invention as combination therapy is generally more effective than the use of single anti-neoplastic agents. Thus, a further aspect of the present invention provides compositions containing a therapeutically effective amount of at least one invention salinosporamide compound in combination with at least one other anti-neoplastic agent. Such compositions can also be provided together with physiologically tolerable liquid, gel or solid carriers, diluents, adjuvants and excipients. Such carriers, diluents, adjuvants and excipients may be found in the United States Pharmacopeia Vol. XXII and National Formulary Vol XVII, U.S. Pharmacopeia Convention, Inc., Rockville, Md. (1989), the contents of which are herein incorporated by reference. Additional modes of treatment are provided in AHFS Drug Information, 1993 ed. by the American Hospital Formulary Service, pp. 522–660, the contents of which are herein incorporated by reference.

Anti-neoplastic agents which may be utilized in combination with an invention salinosporamide compound include those provided in The Merck Index, 11th ed. Merck & Co., Inc. (1989) pp. Ther 16–17, the contents of which are hereby incorporated by reference. In a further embodiment of the invention, anti-neoplastic agents may be antimetabolites which may include, but are not limited to, methotrexate, 5-fluorouracil, 6-mercaptopurine, cytosine arabinoside, hydroxyurea, and 2-chlorodeoxyadenosine. In another embodiment of the present invention, the anti-neoplastic agents contemplated are alkylating agents which may include, but are not limited to, cyclophosphamide, melphalan, busulfan, paraplatin, chlorambucil, and nitrogen mustard. In a further embodiment of the invention, the antineoplastic agents are plant alkaloids which may include, but are not limited to, vincristine, vinblastine, taxol, and etoposide. In a further embodiment of the invention, the anti-neoplastic agents contemplated are antibiotics which may include, but are not limited to, doxorubicin (adriamycin), daunorubicin, mitomycin c, and bleomycin. In a further embodiment of the invention, the anti-neoplastic agents contemplated are hormones which may include, but are not limited to, calusterone, diomostavolone, propionate, epitiostanol, mepitiostane, testolactone, tamoxifen, polyestradiol phosphate, megesterol acetate, flutamide, nilutamide, and trilotane. In a further embodiment of the invention, the anti-neoplastic agents contemplated include enzymes which may include, but are not limited to, L-Asparaginase or aminoacridine derivatives which may include, but are not limited to, amsacrine. Additional anti-neoplastic agents include those provided in Skeel, Roland T., "Antineoplastic Drugs and Biologic Response Modifier: Classification, Use and Toxicity of Clinically Useful Agents," Handbook of Cancer Chemotherapy (3rd ed.), Little Brown & Co. (1991), the contents of which are herein incorporated by reference.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated.

The term "therapeutically effective amount" means the amount of the subject compound that will elicit the biological or medical response of a tissue, system, animal or human that is being sought by the researcher, veterinarian, medical doctor or other clinician, e.g., lessening of the effects/symptoms of cell proliferative disorders.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention to the individual in need of treatment. Administration of the invention compounds can be prior to, simultaneously with, or after administration of another therapeutic agent or other anti-neoplastic agent.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed.

Compounds and compositions of the invention can be administered to mammals for veterinary use, such as for domestic animals, and clinical use in humans in a manner similar to other therapeutic agents. In general, the dosage required for therapeutic efficacy will vary according to the type of use and mode of administration, as well as the particularized requirements of individual hosts. Ordinarily, dosages will range from about 0.001 to 1000 μg/kg, more usually 0.01 to 10 μg/kg, of the host body weight. Alternatively, dosages within these ranges can be administered by constant infusion over an extended period of time, usually exceeding 24 hours, until the desired therapeutic benefits have been obtained. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The invention will now be described in greater detail by reference to the following non-limiting examples.

EXAMPLES

Methods and Materials

HPLC-Purification of invention compounds was accomplished by RP-MPLC on C18-solid phase (Aldrich) using a step gradient on Kontes Flex-columns (15×7 mm). Semi-preparative HPLC was performed on an isocratic HPLC system with a Waters pump 6000H on normal phase column Si-Dynamas-60 Å (250×5 mm) or reversed phase column C18-Dynamax-60 Å, flow 2 mL/minute, with a differential refractomeric detector Waters R401.

LC-MS-The LC-MS chromatography was performed on a Hewlett-Packard system series HP1100 with DAD and MSD1100 detection. The separation was accomplished on reversed phase C18 (Agilent Hypersil ODS 5 μm, column dimension 4.6×100 mm), flow rate 0.7 mL/minute using a standard gradient: 10% acetonitrile, 15 minutes; 98% acetonitrile (Burdick & Jackson high purity solvents). The MS-detection was in ESI positive mode, capillary voltage 3500 eV, fragmentation voltage 70 eV, mass range m/z 100–1000. The APCI-mode was measured at a flow rate of 0.5 mL/minute, positive detection, capillary voltage 3000 eV, fragmentation voltage 70 eV.

NMR-NMR spectra were measured on a Varian 300 MHz gradient field spectrometer with inverse-mode for $^1$H or 2D-NMR spectra. The 13C and DEPT spectra were measured on a Varian 400 MHz, broad band instrument. The reference is set on the internal standard tetramethylsilane (TMS, 0.00 ppm).

MS-EI-Low resolution MS-EI spectra were performed on a Hewlett-Packard mass spectrometer with magnetic sector field device, heating rate 20° C./minute up to 320° C., direct injection inlet.

FTMS-MALDI-High resolution MS data were obtained by MALDI operating mode on an IonSpec Ultima FT Mass Spectrometer.

IR-Infrared spectra were measured on a Perkin-Elmer FT infrared spectrophotometer using NaCl windows.

Example 1

Isolation and Characterization of "*Salinsospora*" Species,

Culture Nos. CNB392 and CNB476

Figure 2:
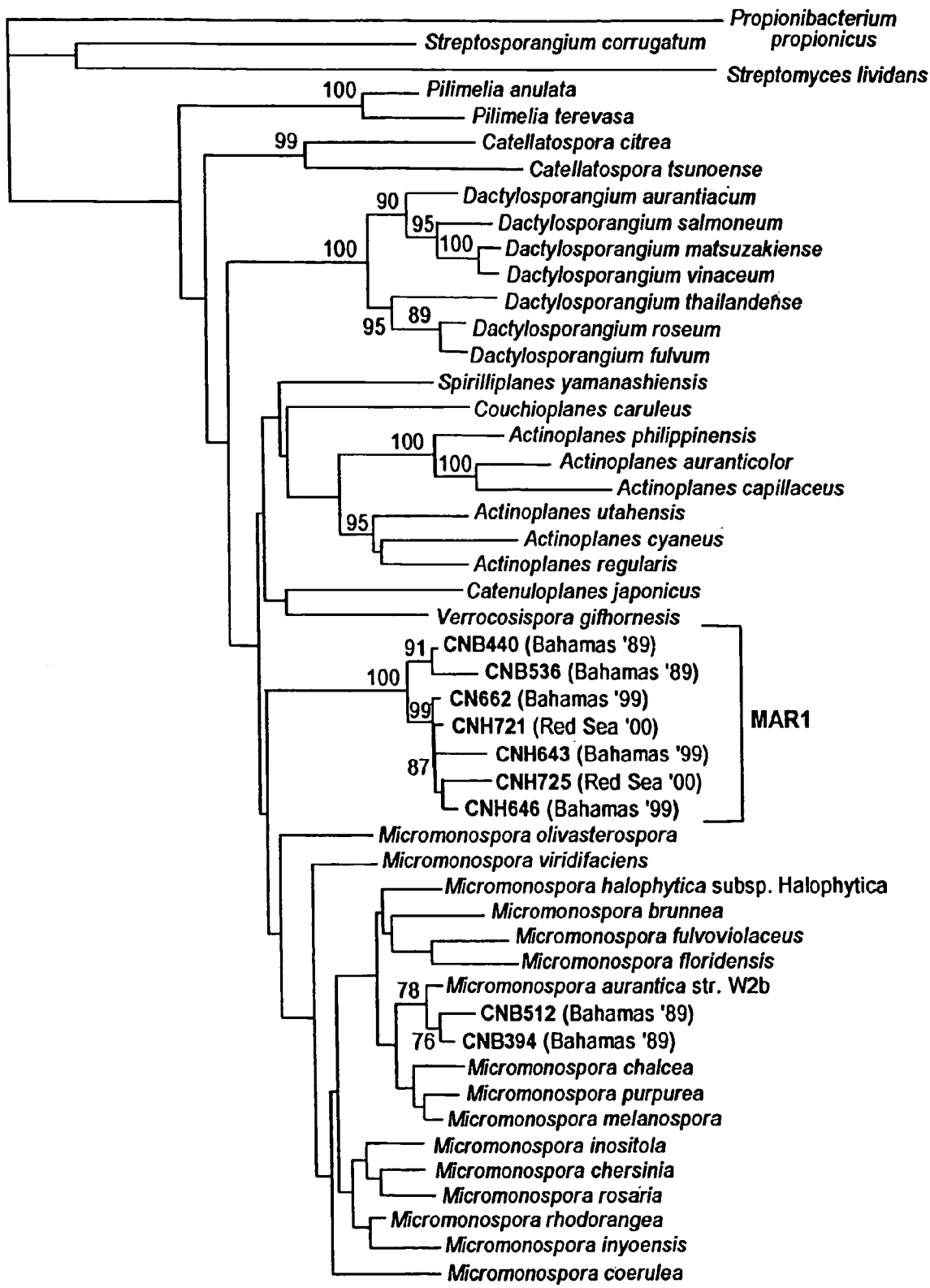
FIG. 2 depicts a phylogenetic tree illustrating the phylogeny of "*Salinospora*".

CNB392 and CNB476 possess signature nucleotides within their 16S rDNA which separate these strains phylogenetically from all other members of the family Micromonosporaceae (see FIG. 15) These signature nucleotides have been determined to be a definitive marker for members of this group which also have a physiological growth requirement of sodium. Signature nucleotides were aligned to *E. coli* positions 27—1492 using all existing members of the Micromonosporaceae in the Ribosomal Database Project as of Jan. 31, 2001. For the "*Salinospora*" clade, 45 partially sequenced morphotypes displayed all the signature nucleotides from positions 207–468. The seven "*Salinospora*" isolates sequenced almost in their entirety (see FIG. 2) displayed all of the signatures in FIG. 15.

The strains CNB392 and CNB476 form bright orange to black colonies on agar and lacks aerial mycelia. Dark brown and bright orange diffusible pigments are produced depending upon cellular growth stage. Spores blacken the colony surface and are borne on substrate mycelia. Vegetative mycelia are finely branched and do not fragment. Spores are produced singly or in clusters. Neither sporangia nor spore motility has been observed for these strains. CNB392 and CNB476 have an obligate growth requirement for sodium and will not grow on typical media used for maintenance of other generic members of the Micromonosporaceae. CNB392 and CNB476 have been found to grow optimally on solid media TCG or M1 at 30° C.

| TCG | 3 grams tryptone<br>5 grams casitone<br>4 grams glucose<br>18 grams agar (optional)<br>1 liter filtered seawater | M1 | 10 grams starch<br>4 grams yeast extract<br>2 grams peptone<br>18 grams agar (optional)<br>1 liter filtered seawater |
|---|---|---|---|

Fermentaion

CNB392 and CNB476 are cultured in shaken AlBfe+C or CKA-liquid media, 1 liter at 35° C. for 9 days. After 4 days 20 grams Amberlite XAD-16 resin (Sigma, nonionic polymeric adsorbent) is added.

| AlBfe + C | 10 grams starch<br>4 grams yeast extract<br>2 grams peptone<br>1 gram $CaCO_3$<br>5 mL KBr (aqueous solution, 20 grams/liter)<br>5 mL $Fe_2(SO_4)_3$ × 4 $H_2O$ (8 grams/liter)<br>1 liter filtered seawater | CKA | 5 grams starch<br>4 mL hydrosolubles (50%)<br>2 grams menhaden meal<br>2 grams kelp powder<br>2 grams chitosan<br><br><br>1 liter filtered seawater |
|---|---|---|---|

Extraction

The XAD-16 resin is filtered and the organic extract is eluted with 1 liter ethylacetate followed by 1 liter methanol. The filtrate is then extracted with ethylacetate (3×200 mL). The crude extract from the XAD adsorption is 105 mg. Cytotoxicity on the human colon cancer cell HCT-116 assay is IC50<0.076 μg/mL.

Isolation of Salinosporamide A from CNB392

The crude extract was flash-chromatographed over C18 reversed phase (RP) using a step gradient (FIG. 5). The HCT-116 assay resulted in two active fractions, CNB392-5 and CNB392-6. The combined active fractions (51.7 mg), HCT-116<0.076 μg/mL) were then chromatographed on an isocratic RP-HPLC, using 85% methanol at 2 mL/minute flow as eluent and using refractive index detection. The active fraction CNB392-5/6 (7.6 mg, HCT-116<0.076 μg/mL) was purified on an isocratic normal phase HPLC on silica gel with ethyl acetate:isooctane (9:1) at 2 mL/minute. Salinosporamide A (FIG. 1) was isolated as a colorless, amorphous solid in 6.7 mg per 1 liter yield (6.4%). TLC on silica gel (dichloromethane:methanol 9:1) shows Salinosporamide A at $r_f$=0.6, no UV extinction or fluorescence at 256 nm, yellow with $H_2SO_4$/ethanol, dark red-brown with Godin reagent (vanillin/$H_2SO_4$/$HClO_4$). Salinosporamide A is soluble in $CHCl_3$, methanol, and other polar solvents like DMSO, acetone, acetonitrile, benzene, pyridine, N,N-dimethyformamide, and the like. $^1$H NMR: ($d_5$-pyridine, 300 MHz) 1.37/1.66 (2H, m, $CH_2$), 1.70.2.29 (2H, m, $CH_2$), 1.91 (2H, broad, $CH_2$), 2.07 (3H, s, $CH_3$), 2.32/2.48 (2H, ddd, $^3J$=7.0 Hz, $CH_2$), 2.85 (1H, broad, m, CH), 3.17 (1H, dd, $^3J$=10 Hz, CH), 4.01/4.13 (2H, m, $CH_2$), 4.25 (1H, d, $^3J$=9.0 Hz, CH), 4.98 (1H, broad, OH), 5.88, (1H, ddd, $^3J$=10 Hz, Hz, CH), 6.41 (1H, broad d, $^3J$=10 Hz, CH) 10.62 (1H, s, NH).

$^{13}$C NMR/DEPT: ($d_5$-pyridine, 400 MHz) 176.4 (COOR), 169.0 (CONH), 128.8 (=CH), 128.4 (=CH), 86.1 ($C_q$), 80.2 ($C_q$), 70.9 (CH), 46.2 (CH), 43.2 ($CH_2$), 39.2 (CH), 29.0 ($CH_2$), 26.5 ($CH_2$), 25.3 ($CH_2$), 21.7 ($CH_2$), 20.0 ($CH_3$)

LC-MS (ESI) $t_r$=10.0 minutes, flow 0.7 mL/minute m/z: $(M+H)^+$ 314, $(M+Na)^+$ 336; fragments: $(M+H-CO_2)^+$ 292, $(M+H-CO_2-H_2O)^+$ 270, 252, 204. Cl pattern: $(M+H, 100\%)^+$ 314, $(M+H, 30\%)^+$ 316.

LC MS (APCI): $t_r$=11.7 minutes, flow 0.5 mL/minute m/z: $(M+H)^+$ 314, fragments: $(M+H-CO_2-H_2O)^+$ 270, 252, 232, 216, 160. Cl pattern: $(M+H, 100\%)^+$ 314, $(M+H, 30\%)^+$ 316.

EI: m/z: 269,251, 235, 217, 204, 188 (100%), 160, 152, 138, 126, 110, 81.

FTMS-MALDI: m/z: $(M+H)^+$ 314.1144

FT-IR: ($cm^{-1}$) 2920, 2344, s, 1819 m, 1702 s, 1255, 1085 s, 1020 s, 797 s.

Molecular formula: $C_{15}H_{20}ClNO_4$

Example 2

Bioactivity Assays

Salinosporamide A shows strong activity against human colon cancer cells with an $IC_{50}$ of 0.011 μg/mL (see FIG. 4). The screening on antibacterial or antifungal activity shows no significant activity, see Table 1.

TABLE 1

| Assay | $IC_{50}$ of Salinosporamide A, (μg/mL) |
|---|---|
| HCT-116 | 0.011 |
| Candida albicans | 250 |
| Candida albicans (amphoterocin B resistant) | NSA* |
| Staphylococcus aureus (methecillin resistant) | NSA* |
| Enterococcus faecium (vanomycin resistant) | NSA* |

*NSA = no significant activity

Example 3

Determination of Absolute Stereochemistry

Figure 16:
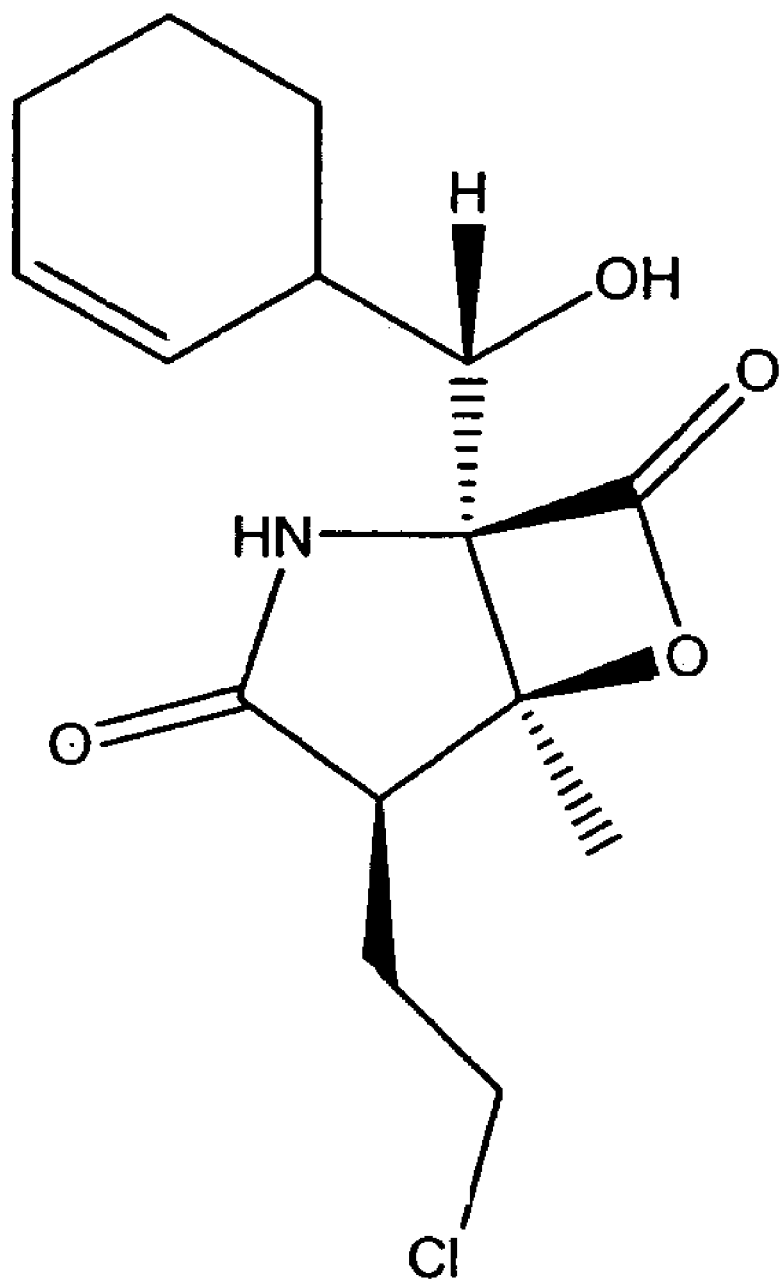
FIG. 16 depicts the chemical structure of an exemplary compound of the invention, salinosporamide A (structure V), with absolute stereochemistry.
Figure 17:
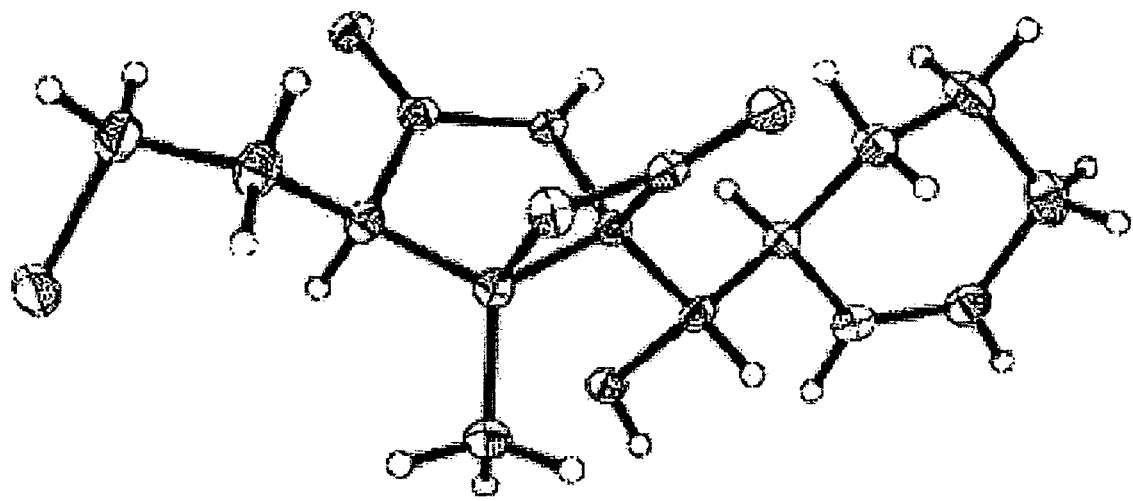
FIG. 17 ORTEP plot of the final X-ray structure of salinosporamide A, depicting the absolute stereochemistry.

Crystallization of a compound of structure I from ethyl acetate/iso-octane resulted in single, cubic crystals, which diffracted as a monoclinic system P2(1). The unusual high unit-cell volume of 3009 Å hosted four independent molecules in which different conformational positions were observed for the flexible chloroethyl substituent. The assignment of the absolute structure from the diffraction anisotropy of the chlorine substituent resolved the absolute stereochemistry of salinosporamide A as 2R,3S,4R,5S,6S (FIGS. 16 and 17) with a Flack parameter of 0.01 and an esd of 0.03.

Although the invention has been described with reference to the above examples, it will be understood that modifications and variations are encompassed within the spirit and scope of the invention. Accordingly, the invention is limited only by the following claims.

What is claimed is:

1. An isolated compound having the structure (I):

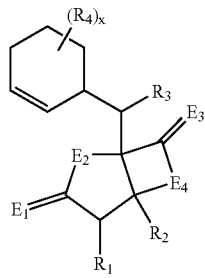

wherein:
- $R_1$ to $R_3$ are each independently —H, alkyl, substituted alkyl, alkenyl, substituted alkenyl, alkynyl, substituted alkynyl, aryl, substituted aryl, heteroaryl, substituted heteroaryl, heterocyclic, substituted heterocyclic, cycloalkyl, substituted cycloalkyl, alkoxy, substituted alkoxy, thioalkyl, substituted thioalkyl, hydroxy, halogen, amino, amido, carboxyl, —C(O)H, acyl, oxyacyl, carbamate, sulfonamide, or sulfuryl,
- Each $R_4$ is independently alkyl, substituted alkyl, alkenyl, substituted alkenyl, alkynyl, substituted alkynyl, aryl, substituted aryl, cycloalkyl, substituted cycloalkyl;
- $E_1$ to $E_4$ are each independently —O, —$NR_5$, or —S, wherein $R_5$ is —H or $C_1$–$C_6$ alkyl; and
- X is 0 to 8.

2. The compound of claim 1, wherein $E_1$, $E_3$, and $E_4$ are —O, and $E_2$ is —NH.

3. The compound of claim 1, wherein $R_1$ and $R_2$ are —H, alkyl, or substituted alkyl, and $R_3$ is hydroxy or alkoxy.

4. The compound of claim 1, wherein $R_1$ is a substituted alkyl.

5. The compound of claim 4, wherein the substituted alkyl is a halogenated alkyl.

6. The compound of claim 5, wherein the halogenated alkyl is a chlorinated alkyl.

7. The compound of claim 6, wherein the compound has the structure (IV):

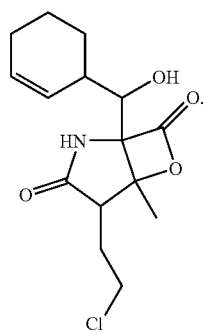

8. The compound of claim 7, wherein the compound has the structure:

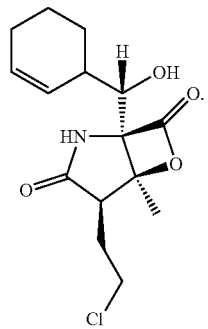

9. A pharmaceutical composition comprising at least one compound of claim 1 in a pharmaceutically acceptable carrier therefor.

10. A pharmaceutical composition, comprising an effective amount of a pharmaceutically acceptable carrier and a compound of claim 1.

11. The pharmaceutical composition of claim 10, further comprising at least one additional anti-neoplastic agent.

12. A pharmaceutical composition, comprising an effective amount of a pharmaceutically acceptable carrier and a compound having the structure:

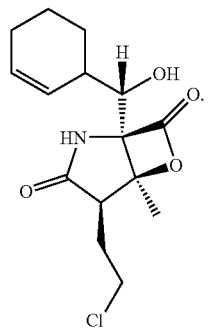

13. A pharmaceutical composition useful for inhibiting proliferation of mammalian colon cancer cells, comprising an effective amount of a pharmaceutically acceptable carrier and a compound of claim 1.

14. The pharmaceutical composition of claim 13, further comprising at least one additional anti-neoplastic agent.

15. A pharmaceutical composition useful for inhibiting proliferation of mammalian colon cancer cells, comprising an effective amount of a pharmaceutically acceptable carrier and a compound having the structure:

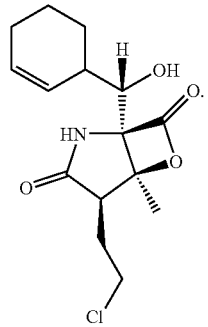

* * * * *

UNITED STATES PATENT AND TRADEMARK OFFICE
CERTIFICATE OF CORRECTION

| | | |
|---|---|---|
| PATENT NO. | : 7,176,232 B2 | Page 1 of 1 |
| APPLICATION NO. | : 10/838157 | |
| DATED | : February 13, 2007 | |
| INVENTOR(S) | : Fenical et al. | |

It is certified that error appears in the above-identified patent and that said Letters Patent is hereby corrected as shown below:

COLUMN 1, LINE 20

Delete "may have"

and replace with --has--

Signed and Sealed this

Third Day of July, 2007

JON W. DUDAS
*Director of the United States Patent and Trademark Office*